US011446309B2

(12) United States Patent
Bradner et al.

(10) Patent No.: US 11,446,309 B2
(45) Date of Patent: Sep. 20, 2022

(54) COMBINATION THERAPY FOR CANCER USING BROMODOMAIN AND EXTRA-TERMINAL (BET) PROTEIN INHIBITORS

(71) Applicant: Dana-Farber Cancer Institute, Inc., Boston, MA (US)

(72) Inventors: James E. Bradner, Weston, MA (US); Michael R. McKeown, Brookline, MA (US); Margaret A. Shipp, Wellesley, MA (US); Bjoern Chapuy, Boston, MA (US); Kwok-kin Wong, Arlington, MA (US); Zhao Chen, Sharon, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/034,922

(22) PCT Filed: Nov. 7, 2014

(86) PCT No.: PCT/US2014/064549
§ 371 (c)(1),
(2) Date: May 6, 2016

(87) PCT Pub. No.: WO2015/070020
PCT Pub. Date: May 14, 2015

(65) Prior Publication Data
US 2016/0279141 A1    Sep. 29, 2016

Related U.S. Application Data

(60) Provisional application No. 61/901,908, filed on Nov. 8, 2013.

(51) Int. Cl.
| | |
|---|---|
| *A61K 31/551* | (2006.01) |
| *C07D 487/04* | (2006.01) |
| *C07D 495/14* | (2006.01) |
| *A61K 31/404* | (2006.01) |
| *A61K 31/453* | (2006.01) |
| *A61K 31/5377* | (2006.01) |
| *A61K 45/06* | (2006.01) |
| *A61P 35/00* | (2006.01) |

(52) U.S. Cl.
CPC .......... *A61K 31/551* (2013.01); *A61K 31/404* (2013.01); *A61K 31/453* (2013.01); *A61K 31/5377* (2013.01); *A61K 45/06* (2013.01); *A61P 35/00* (2018.01); *C07D 487/04* (2013.01); *C07D 495/14* (2013.01)

(58) Field of Classification Search
CPC .............. A61K 31/404; A61K 31/453; A61K 31/5377; A61K 31/551; A61K 45/06; A61P 35/00; A61P 43/00; C07D 487/04; C07D 495/14
See application file for complete search history.

(56) References Cited

U.S. PATENT DOCUMENTS

| | | |
|---|---|---|
| 2,951,540 A | 9/1960 | Hawkins |
| 3,681,343 A | 8/1972 | Hester, Jr. |
| 3,709,898 A | 1/1973 | Hester, Jr. |
| 3,812,259 A | 5/1974 | Collins |
| 4,621,083 A | 11/1986 | Casals-Stenzel et al. |
| 5,104,543 A | 4/1992 | Brandt et al. |
| 5,593,988 A | 1/1997 | Tahara et al. |
| 5,712,274 A | 1/1998 | Sueoka et al. |
| 5,721,231 A | 2/1998 | Moriwaki et al. |
| 5,753,649 A | 5/1998 | Tahara et al. |
| 5,760,032 A | 6/1998 | Kitajima et al. |
| 5,846,972 A | 12/1998 | Buckman et al. |
| 5,854,238 A | 12/1998 | Kempen |
| 6,312,215 B1 | 11/2001 | Walker |
| 6,444,664 B1 | 9/2002 | Princen et al. |
| 6,861,422 B2 | 3/2005 | Hoffmann et al. |
| 7,015,213 B1 | 3/2006 | Bigg et al. |
| 7,528,143 B2 | 5/2009 | Noronha et al. |
| 7,528,153 B2 | 5/2009 | Aerts |
| 7,589,167 B2 | 9/2009 | Zhou et al. |
| 7,750,152 B2 | 7/2010 | Hoffman et al. |
| 7,786,299 B2 | 8/2010 | Hoffmann et al. |
| 7,816,530 B2 | 10/2010 | Grauert |
| 7,825,246 B2 | 11/2010 | Noronha et al. |
| 8,003,786 B2 | 8/2011 | Hoffmann et al. |
| 8,044,042 B2 | 10/2011 | Adachi et al. |
| 8,133,900 B2 | 3/2012 | Hood et al. |
| 8,138,199 B2 | 3/2012 | Noronha et al. |
| 8,338,464 B2 | 12/2012 | Melnick et al. |
| 8,476,260 B2 | 7/2013 | Miyoshi et al. |
| 8,604,042 B2 | 12/2013 | Noronha et al. |

(Continued)

FOREIGN PATENT DOCUMENTS

| | | |
|---|---|---|
| CA | 2020806 A1 | 1/1991 |
| CA | 2710740 A1 | 7/2009 |

(Continued)

OTHER PUBLICATIONS

Mertz et al. 2011, PNAS, vol. 108, No. 40 pp. 16669-16674.*
Souers et al. Feb. 2013, Nature Medicine, vol. 19, No. 2, pp. 202-210.*
Wass et al. Blood, 2012, vol. 120, No. 21, p. 4862.*
Lee et al. May 2009, Cancer Sci., vol. 100, No. 5, pp. 920-926. (Year: 2009).*
*Final Rejection for U.S. Appl. No. 13/697,963, "Compositions and Methods for Modulating Metabolism," dated Aug. 21, 2015.
*Final Rejection for U.S. Appl. No. 13/697,963, "Compositions and Methods for Modulating Metabolism," dated Jan. 18, 2017.
*Final Rejection for U.S. Appl. No. 13/934,843, "Compositions and Methods for Treating Leukemia," dated Oct. 30, 2015.

(Continued)

Primary Examiner — Kara R McMillian
(74) Attorney, Agent, or Firm — Foley Hoag LLP

(57) ABSTRACT

The present invention provides methods for treating cancer using combinations of bromodomain and extra-terminal (BET) protein inhibitors and certain chemotherapeutic drugs.

6 Claims, 9 Drawing Sheets

(56) References Cited

U.S. PATENT DOCUMENTS

| | | | |
|---|---|---|---|
| 8,981,083 | B2 | 3/2015 | Bradner et al. |
| 9,301,962 | B2 | 4/2016 | Bradner et al. |
| 9,320,711 | B2 | 4/2016 | Natoli et al. |
| 9,320,741 | B2 | 4/2016 | Bradner et al. |
| 9,763,956 | B2 * | 9/2017 | Bernstein ............... A61K 45/06 |
| 9,789,120 | B2 | 10/2017 | Bradner et al. |
| 9,815,849 | B2 | 11/2017 | Bradner et al. |
| 10,124,009 | B2 | 11/2018 | Landau et al. |
| 10,407,441 | B2 | 9/2019 | Bradner et al. |
| 10,676,484 | B2 | 6/2020 | Bradner et al. |
| 10,813,939 | B2 | 10/2020 | Sotomayor et al. |
| 10,925,881 | B2 | 2/2021 | Landau et al. |
| 2002/0032200 | A1 | 3/2002 | Cai et al. |
| 2002/0169158 | A1 | 11/2002 | Hunt et al. |
| 2003/0130268 | A1 | 7/2003 | Sagara et al. |
| 2003/0216758 | A1 | 11/2003 | Signore |
| 2004/0043378 | A1 | 3/2004 | Zhou et al. |
| 2004/0176380 | A1 | 9/2004 | Hoffmann et al. |
| 2006/0074088 | A1 | 4/2006 | Munzert et al. |
| 2006/0142257 | A1 | 6/2006 | Nieschlag et al. |
| 2006/0223055 | A1 | 10/2006 | Howley et al. |
| 2007/0105839 | A1 | 5/2007 | Imbach et al. |
| 2007/0111933 | A1 | 5/2007 | Kopchick et al. |
| 2007/0179178 | A1 | 8/2007 | Buettelmann et al. |
| 2007/0218135 | A1 | 9/2007 | Mukharya et al. |
| 2007/0289310 | A1 | 12/2007 | Dooley et al. |
| 2008/0004308 | A1 | 1/2008 | Dhanak et al. |
| 2008/0081781 | A1 | 4/2008 | Lippa et al. |
| 2008/0305113 | A1 | 12/2008 | Kwon et al. |
| 2009/0012064 | A1 | 1/2009 | Sagara et al. |
| 2009/0238828 | A1 | 9/2009 | Munzert et al. |
| 2009/0280115 | A1 | 11/2009 | Maier et al. |
| 2009/0281191 | A1 | 11/2009 | Rangwala et al. |
| 2010/0041643 | A1 | 2/2010 | Adachi et al. |
| 2010/0227838 | A1 | 9/2010 | Shah et al. |
| 2010/0249412 | A1 | 9/2010 | Linz et al. |
| 2010/0286127 | A1 | 11/2010 | Miyoshi et al. |
| 2011/0028405 | A1 | 2/2011 | Harrison et al. |
| 2011/0098288 | A1 | 4/2011 | Major et al. |
| 2011/0143651 | A1 | 6/2011 | Marocchi et al. |
| 2011/0172231 | A1 | 7/2011 | Baenteli et al. |
| 2011/0201606 | A1 | 8/2011 | Garcia-Echeverria et al. |
| 2011/0212077 | A1 | 9/2011 | Noronha et al. |
| 2011/0245245 | A1 | 10/2011 | Mortensen et al. |
| 2012/0014979 | A1 | 1/2012 | Dent |
| 2012/0040961 | A1 | 2/2012 | Gray et al. |
| 2012/0202798 | A1 | 8/2012 | Sagara et al. |
| 2012/0244209 | A1 | 9/2012 | Roth et al. |
| 2012/0329803 | A1 | 12/2012 | Linz et al. |
| 2013/0184264 | A1 | 7/2013 | Bradner et al. |
| 2013/0210813 | A1 | 8/2013 | Bradner et al. |
| 2013/0245013 | A1 | 9/2013 | Mohr et al. |
| 2013/0252331 | A1 | 9/2013 | Bradner et al. |
| 2013/0261109 | A1 | 10/2013 | Miyoshi et al. |
| 2013/0274239 | A1 | 10/2013 | Gangloff et al. |
| 2013/0280332 | A1 | 10/2013 | Moss et al. |
| 2014/0011862 | A1 | 1/2014 | Bradner et al. |
| 2014/0243322 | A1 | 8/2014 | Arnold et al. |
| 2015/0054642 | A1 | 2/2015 | Carruthers |
| 2015/0335656 | A1 | 11/2015 | Miyoshi et al. |
| 2016/0033519 | A1 | 2/2016 | Bradner et al. |
| 2016/0168154 | A1 | 6/2016 | Marineau et al. |
| 2016/0231314 | A1 | 8/2016 | Ryan et al. |
| 2016/0256458 | A1 | 9/2016 | Bair et al. |
| 2016/0279141 | A1 | 9/2016 | Bradner et al. |
| 2016/0332993 | A1 | 11/2016 | Bradner et al. |
| 2016/0347749 | A1 | 12/2016 | Bradner et al. |
| 2017/0008895 | A1 | 1/2017 | Bradner et al. |
| 2017/0029437 | A1 | 2/2017 | Bradner et al. |
| 2017/0209461 | A1 | 7/2017 | Landau et al. |
| 2017/0333444 | A1 | 11/2017 | Landau et al. |
| 2017/0360801 | A1 * | 12/2017 | Sotomayor ......... A61K 31/5517 |
| 2018/0193350 | A1 | 7/2018 | Landau et al. |
| 2018/0222917 | A1 | 8/2018 | Bradner et al. |
| 2018/0237454 | A1 | 8/2018 | Bradner et al. |
| 2020/0148702 | A1 | 5/2020 | Bradner et al. |

FOREIGN PATENT DOCUMENTS

| | | |
|---|---|---|
| CH | 622019 A5 | 3/1981 |
| CN | 1227555 A | 9/1999 |
| CN | 100348600 C | 11/2007 |
| CN | 101910182 A | 12/2010 |
| CN | 103037865 A | 4/2013 |
| DE | 3724164 A1 | 1/1988 |
| EP | 0 087 850 A1 | 9/1983 |
| EP | 0 368 175 A1 | 5/1990 |
| EP | 0 387 613 A1 | 9/1990 |
| EP | 0 934 940 A1 | 8/1999 |
| EP | 0 989 131 A1 | 3/2000 |
| EP | 1 297 836 A1 | 4/2003 |
| EP | 1 887 008 A1 | 2/2008 |
| EP | 2 239 264 A1 | 10/2010 |
| FR | 2329668 A1 | 5/1977 |
| JP | 1 -299231 | 12/1989 |
| JP | 6-157316 | 6/1994 |
| JP | H10500998 A | 1/1998 |
| JP | 11-228576 | 8/1999 |
| JP | 11-512107 | 10/1999 |
| JP | 3001979 B2 | 1/2000 |
| JP | 3096299 B2 | 10/2000 |
| JP | 2006519236 A | 8/2006 |
| JP | 2008/156311 A | 7/2008 |
| JP | 2013510123 A | 3/2013 |
| JP | 2013/532130 A | 8/2013 |
| JP | 5913292 B2 | 4/2016 |
| JP | 61-87684 B2 | 8/2017 |
| KR | 10-2000-0016732 | 3/2000 |
| RU | 2294761 C2 | 3/2007 |
| TW | 201217382 A | 5/2012 |
| WO | WO-97/13537 A1 | 4/1997 |
| WO | WO-97/37705 A1 | 10/1997 |
| WO | WO-97/47622 A1 | 12/1997 |
| WO | WO-98/11111 A1 | 3/1998 |
| WO | WO-99/34850 A1 | 7/1999 |
| WO | WO-01/95912 A1 | 12/2001 |
| WO | WO-2006/129623 A1 | 12/2006 |
| WO | WO-2007/056117 A1 | 5/2007 |
| WO | WO-2007/095188 A2 | 8/2007 |
| WO | WO-2008/083056 A2 | 7/2008 |
| WO | WO-2008/137081 A1 | 11/2008 |
| WO | WO-2009/084693 A1 | 7/2009 |
| WO | WO-2010/015387 A1 | 2/2010 |
| WO | WO-2010/049466 A1 | 5/2010 |
| WO | WO-2011/054553 A1 | 5/2011 |
| WO | WO-2011/054841 A1 | 5/2011 |
| WO | WO-2011/054843 A1 | 5/2011 |
| WO | WO-2011/054844 A1 | 5/2011 |
| WO | WO-2011/054845 A1 | 5/2011 |
| WO | WO-2011/054846 A1 | 5/2011 |
| WO | WO-2011/054848 A1 | 5/2011 |
| WO | WO-2011/143651 A1 | 11/2011 |
| WO | WO-2011/143657 A1 | 11/2011 |
| WO | WO-2011/143660 A2 | 11/2011 |
| WO | WO 2011/143669 A2 * | 11/2011 |
| WO | WO-2011/143669 A2 | 11/2011 |
| WO | WO-2011/161031 A1 | 12/2011 |
| WO | WO-2011/162845 A1 | 12/2011 |
| WO | WO-2012/050907 A2 | 4/2012 |
| WO | WO-2012/075383 A2 | 6/2012 |
| WO | WO-2012/075456 A1 | 6/2012 |
| WO | WO-2012/095505 A1 | 7/2012 |
| WO | WO-2012/116170 A1 | 8/2012 |
| WO | WO-2012/118812 A2 | 9/2012 |
| WO | WO-2013/019710 A1 | 2/2013 |
| WO | WO-2013/030150 A | 3/2013 |
| WO | WO-2013/030450 A1 | 3/2013 |
| WO | WO-2013/033268 A2 | 3/2013 |
| WO | WO-2013/033269 A1 | 3/2013 |
| WO | WO-2013/033270 A2 | 3/2013 |
| WO | WO-2013/033420 A1 | 3/2013 |
| WO | WO-2013/097601 A1 | 7/2013 |

(56) References Cited

FOREIGN PATENT DOCUMENTS

| | | |
|---|---|---|
| WO | WO-2013/148197 A1 | 10/2013 |
| WO | WO 2013/192274 A2 * | 12/2013 |
| WO | WO-2014/068402 A2 | 5/2014 |
| WO | WO-2014/071247 A1 | 5/2014 |
| WO | WO-2014/128070 A1 | 8/2014 |
| WO | WO-2014/128111 A1 | 8/2014 |
| WO | WO-2014/134583 A2 | 9/2014 |
| WO | WO-2014/144721 A2 | 9/2014 |
| WO | WO-2014/159392 A1 | 10/2014 |
| WO | WO-2014/193951 A1 | 12/2014 |
| WO | WO-2015/018521 A1 | 2/2015 |
| WO | WO-2015/018522 A1 | 2/2015 |
| WO | WO-2015/023938 A1 | 2/2015 |
| WO | WO-2015/054642 A2 | 4/2015 |
| WO | WO-2015/070020 A2 | 5/2015 |
| WO | WO-2015/081284 A1 | 6/2015 |
| WO | WO-2015/100282 A1 | 7/2015 |
| WO | WO-2015/131113 A1 | 9/2015 |
| WO | WO-2016/069578 A1 | 5/2016 |
| WO | WO-2016/210275 A1 | 12/2016 |
| WO | WO-2017/059319 A2 | 4/2017 |

OTHER PUBLICATIONS

*Non-Final Rejection for U.S. Appl. No. 13/697,963, "Compositions and Methods for Modulating Metabolism," dated May 31, 2016.
*Non-Final Rejection for U.S. Appl. No. 13/934,843, "Compositions and Methods for Treating Leukemia," dated Jan. 25, 2017.
*Non-Final Rejection for U.S. Appl. No. 14/977,343, "Male Contraeptive Compositions and Methods of Use," dated Aug. 24, 2016.
*Non-Final Rejection for U.S. Appl. No. 15/061,576, "Compositions and Methods for Treating Neoplasia, Inflammatory Disease and Other Disorders," dated Aug. 2, 2017.
*Non-Final Rejection for U.S. Appl. No. 15/121,964, "Treatment of Conditions Associated with Hyperinsulinaemia," dated Oct. 4, 2017.
*Notice of Allowance for U.S. Appl. No. 14/977,343, "Male Contraeptive Compositions and Methods of Use," dated Jun. 16, 2017.
*Notice of Allowance for U.S. Appl. No. 13/698,006, "Male Contraceptive Compositions and Methods of Use," dated Sep. 3, 2015.
*Notice of Allowance for U.S. Appl. No. 13/934,843 dated Jul. 13, 2017.
*Notice of Allowance for U.S. Appl. No. 14/977,343, "Male Contraeptive Compositions and Methods of Use," dated Feb. 13, 2017.
*Notice of Allowance, U.S. Appl. No. 13/698,010, dated Aug. 21, 2014.
*Notice of Allowance, U.S. Appl. No. 14/502,840, dated Dec. 4, 2015.
*Office Action, U.S. Appl. No. 13/697,963, dated Nov. 21, 2014.
*Office Action, U.S. Appl. No. 13/698,006, dated Apr. 10, 2014.
*Office Action, U.S. Appl. No. 13/698,006, dated Oct. 23, 2014.
*Office Action, U.S. Appl. No. 13/698,006, Dated: Sep. 26, 2013.
* Office Action, U.S. Appl. No. 13/934,843, Dated: Mar. 23, 2015.
*Office Action, U.S. Appl. No. 15/522,222, dated Mar. 2, 2018.
Requirement for Restriction/Election for U.S. Appl. No. 13/697,963, "Compositions and Methods for Modulating Metabolism," dated Mar. 20, 2014.
Requirement for Restriction/Election for U.S. Appl. No. 13/934,843, "Compositions and Methods for Treating Leukemia," dated Jul. 1, 2014.
*"Requirement for Restriction/Election for U.S. Appl. No. 15/061,576, "Compositions and Methods for Treating Neoplasia, Inflammatory Disease and Other Disorders," dated Feb. 15, 2017.
Abbate, et al., "Structure of the papillomavirus DNA-tethering complex E2:Brd4 and a peptide that ablates HPV chromosomal association," Mol Cell, 24(6): 877-889, (2006).
Acosta et al., "Amifostine Impairs p53-mediated Apoptosis of Human Myeloid Leukemia Cells," Molecular Cancer Therapeutics, 2: 893-900 (2003).

Anders et al., "Genome-wide Localization of Small Molecules," Nat Biotechnol, 32(1): 92-96 (2014).
Arango, et al., "Reversible Azoospermia in a Patient Treated with Triazolam," Eur J Contracept Reprod Health Care, 1(3): 293-294 (1996).
Bartholomeeusen et al., "Bromodomain and Extra-terminal (BET) Bromodomain Inhibition Activate Transcription via Transient Release of Positive Transcription Elongation Factor b (P-TEFb) from 7SK Small Nuclear Ribonucleoprotein," J Biol Chem, 287(43): 36609-36619 (2012).
Baud et al., "Chemical Biology. A Bump-and-hole Approach to Engineer Controlled Selectivity of BET Bromodomain Chemical Probes," Science, 346(6209): 638-641 (2014).
Berge et al., "Pharmaceutical Salts," J Pharm Sci, 66(1): 1-19 (1977).
Berkovits, et al., "The First Bromodomain of the Testis-Specific Double Bromodomain Protein Brdt is Required for Chromocenter Organization That is Modulated by Genetic Background," Dev Biol, 360(2): 358-368 (2011).
Berkovits, et al., "The Role of the Double Bromodomain-Containing BET Genes During Mammalian Spermatogenesis," Curr Top Dev Biol, 102: 293-326 (2013).
Buchdunger, et al., "Inhibition of the Abl Protein-Tyrosine Kinase In Vitro And In Vivo By a 2-Phenylaminopyrimidine Derivative," Cancer Res, 56(1): 100-104 (1996).
Buchdunger, et al., "Selective inhibition of the platelet-derived growth factor signal transduction pathway by a protein-tyrosine kinase inhibitor of the 2-phenylaminopyrimidine class," Proc Natl Acad Sci, 92(7): 2558-2562 (1995).
Bullock, et al., "Structural basis of Inhibitor Specificity of the Human Protooncogene Proviral Insertion site in Moloney Murine ILeukemia virus (PIM-1) kinase," J Med Chern, 48(24): 7604-7614 (2005).
Cellai, et al., "Mechanistic Insight Into WEB-2170-induced Apoptosis in Human Acute Myelogenous Leukemia Cells: the Crucial Role of PTEN," Exp Hematol, 37(10): 1176-1185 (2009).
Cellai, et al., "Specific PAF Antagonist WEB-2086 Induces Terminal Differentiation of Murine and Human Leukemia Cells," FASEB, 16(7): 733-735 (2002).
Chaidos et al., "Protent Antimyeloma Activity of the Novel Bromodomain Inhibitors I-BET151 and I-BET762," Blood, 123(5): 697-705 (2014).
Cheng et al., "Adjudin Disrupts Spermatogenesis via the Action of Some Unlikely Partners: Eps8, Arp2/3 complex, drebrin E, PAR6 and 14-3-3," Spermatogenesis, 1(4): 291-297 (2011).
Chesi et al., "Drug Response in a Genetically Engineered Mouse Model of Multiple Myeloma is Predictive of Clinical Efficacy," Blood, 120(2): 376-385 (2012).
Choi et al., "Brain Penetrant LRRK2 Inhibitor," ACS Med Chem Lett, 3(8): 658-662 (2012).
Cole, "Chemical probes for histone-modifying enzymes," Nat Chem Biol, 4: 590-597 (2008).
Crawford, et al., "Bromodomain 4 activation predicts breast cancer survival," Proc Natl Acad Sci, 105(17): 6380-6385 (2008).
Dawson et al., "Inhibition of BET Recruitment to Chromatin as an Effective Treatment for MLL-fusion Leukaemia," Nature, 478(7370): 529-533 (2011).
Delbroek et al., "Development of an Enzyme-linked Immunosorbent Assay for Detection of Cellular and in Vivo LRRK2 S935 Phosphorylation," J Pharm Biomed Anal, 76: 49-58 (2013).
Delmore et al., "BET Bromodomain Inhibition as a Terapeutic Strategy to Target c-Myc," cell, 146(6): 904-917 (2011).
Deng et al., "Structural Determinants for ERK5 (MAPK7) and Leucine Rich Repeat Kinase 2 Activities of Benzo[e]pyrimido-[5,4-b]diazepine-6(11H)-ones," Eur J Med Chem, 70: 758-767 (2013).
Denis, et al., "An Emerging Role for Bromodomain-Containing Proteins in Chromatin Regulation and Transcriptional Control of Adipogenesis," FEBS Lett, 584(15): 3260-3268 (2010).
Dey, et al., "Brd4 Marks Select Genes of Mitotic Chromatin and Directs Postmitotic Transcription," Mol Biol Cell, 20(23): 4899-4909 (2009).

(56) References Cited

OTHER PUBLICATIONS

Diamanti-Kandarakis et al., "Therapeutic Effects of Metformin on Insulin Resistance and Hyperandrogenism in Polycystic Ovary Syndrome," European Journal of Endocrinology, 138: 269-274 (1998).
Druker, et al., "Effects of a selective inhibitor of the Abl Tyrosine kinase on the Growth of Bcr-Abl positive cells," Nat Med, 2(5): 561-566 (1996).
Druker, et al., "Efficacy and safety of a specific inhibitor of the BCR-ABL tyrosine kinase in chronic myeloid leukemia," N Engl J Med, 344:1031-1037 (2001).
Elkins et al., "X-ray Crystal Structure of ERK5 (MAPK7) in Complex with a Specific Inhibitor," J Med Chem, 56(11): 4413-4421 (2013).
Examination Report, AU Application No. 2011252808, dated: Aug. 5, 2013.
Extended European Search Report for European Patent Application No. 14860080.2 dated May 3, 2017.
Extended European Search Report for PCT/US2014/048230, dated Jan. 31, 2017.
Fedorov, et al., "A Systematic Interaction Map of Validated Kinase Inhibitors with Ser/Thr kinases," Proc Natl Acad Sci, 104(51): 20523-20528 (2007).
Filippakopoulos et al., "Targeting Bromodomains: Epigenetic Readers of Lysine Acetylation," Nat Rev Drug Discov, 13(5): 337-356 (2014).
Filippakopoulos, et al., "Selective Inhibition of BET Bromodomains," Nature, 468(7327): 1067-1073 (2010).
French, "Demystified Molecular pathology of NUT Midline Carcinomas," J Clin Pathol, 63: 492-496 (2010).
French, et al. "BRD4-NUT Fusion Oncogene: a Novel Mechanism in Aggressive Carcinoma," Cancer Res, 63(2): 304-307 (2003).
French, et al., "BRD-NUT Oncoproteins: a Family of Closely Related Nuclear Proteins that Block Epithelial Differentiation and Maintain the Growth of Carcinoma Cells," Oncogene, 27: 2237-2242 (2008).
French, et al., "BRD4 Bromodomain Gene Rearrangement in Aggressive Carcinoma with Translocation t(15; 19)," Am J Pathol, 159(6): 1987-1992 (2001).
Genbank Submission; NH/NCBI, Accession No. H86170. Hillier et al., Nov. 21, 1995. 2 pages.
Genbank Submission; NH/NCBI, Accession No. NP_001003694. Lubula et al., Oct. 6, 2016. 4 pages.
Genbank Submission; NH/NCBI, Accession No. NP_001420. Ledsaak et al., Sep. 15, 2016. 8 pages.
Genbank Submission; NH/NCBI, Accession No. NP_001717. Barda et al., Feb. 2, 2014. 2 pages.
Genbank Submission; NH/NCBI, Accession No. NP_003061. Agaimy et al., Dec. 10, 2016. 5 pages.
Genbank Submission; NH/NCBI, Accession No. NP_003063. Liao et al., May 2, 2016. 5 pages.
Genbank Submission; NH/NCBI, Accession No. NP_003843. Yuan et al., Dec. 20, 2003. 3 pages.
Genbank Submission; NH/NCBI, Accession No. NP_003875. Li et al., Oct. 7, 2016. 3 pages.
Genbank Submission; NH/NCBI, Accession No. NP_004371. Liu et al., Dec. 10, 2006. 3 pages.
Genbank Submission; NH/NCBI, Accession No. NP_004597. Herzfeld et al., Aug. 26, 2016. 5 pages.
Genbank Submission; NH/NCBI, Accession No. NP_005095. Xiao et al., Oct. 6, 2016. 4 pages.
Genbank Submission; NH/NCBI, Accession No. NP_005753. Dalgaard et al., Oct. 6, 2016. 6 pages.
Genbank Submission; NH/NCBI, Accession No. NP_009168. DiBernardo et al., Sep. 28, 2008. 2 pages.
Genbank Submission; NH/NCBI, Accession No. NP_031397. Shao et al., Jan. 4, 2017. 4 pages.
Genbank Submission; NH/NCBI, Accession No. NP_038478. Jones et al., Sep. 23, 2005. 2 pages.
Genbank Submission; NH/NCBI, Accession No. NP_054828. Hou et al., Sep. 15, 2016. 5 pages.
Genbank Submission; NH/NCBI, Accession No. NP_055392. Aberg et al., Mar. 22, 2014. 3 pages.
Genbank Submission; NH/NCBI, Accession No. NP_060404. Bezrookove et al., Oct. 7, 2016. 5 pages.
Genbank Submission; NH/NCBI, Accession No. NP_060635. Varela et al., Dec. 18, 2011. 3 pages.
Genbank Submission; NH/NCBI, Accession No. NP_060959. Kuryshev et al., Mar. 26, 2006. 2 pages.
Genbank Submission; NH/NCBI, Accession No. NP_061836. Perry et al., Feb. 21, 2016. 7 pages.
Genbank Submission; NH/NCBI, Accession No. NP_066564. Wiper-Bergeron et al., Jun. 3, 2007. 3 pages.
Genbank Submission; NH/NCBI, Accession No. NP_076413. Clark et al., Jun. 27, 2007. 2 pages.
Genbank Submission; NH/NCBI, Accession No. NP_612411. Saare et al., Aug. 25, 2016. 2 pages.
Genbank Submission; NH/NCBI, Accession No. NP_722516. Xia et al., Nov. 22, 2015. 3 pages.
Genbank Submission; NH/NCBI, Accession No. NP_872579. Lee et al., Oct. 6, 2016. 4 pages.
Genbank Submission; NH/NCBI, Accession No. XP_039676. Aug. 19, 2004. 3 pages.
Greenwald, et al., "Eμ-BRD2 Transgenic Mice Develop B-Cell Lymphoma and Leukemia," Blood, 103(4): 1475-1484 (2004).
Haack, et al., "Diagnosis of NUT Midline Carcinoma Using a NUT-specific Monoclonal Antibody," Am J Surg Pathol, 33(7): 984-991 (2009).
He et al., "The Histone Methyltransferase Ezh2 is a Crucial Epigenetic Regulator of Allogeneic T-cell Responses Mediating Graft-versus-host Disease," Blood, 122(25): 119-128 (2013).
Hedrington et al., "Effects of Antecedent GABAA Activation with Alprazolam on Counterregulatory Responses to Hypoglycemia in Healthy Humans," Diabetes, 59(4): 1074-1081 (2010).
Houzelstein et al., "Growth and Early Postimplantation Defects in Mice Deficient for the Bromodomain-containing Protein Brd4," Mol Cell Biol, 22(11): 3794-3802 (2002).
Hsu et al., "Metabolic Syndrome, Hyperinsulinemia and Cancer," The American Journal of Clinical Nutrition, 86(3): 867S-871S (2007).
Hu, et al., "Adjudin Targeting Rabbit Germ Cell Adhesion as a Male Contraceptive: A Pharmacokinetics Study," J Androl, 30(1): 87-93 (2009).
Huang, et al., "Brd4 Coactivates Transcriptional Activation of NF-kB via Specific Binding to Acetylated RelA," Mol Cell Biol, 29(5): 1375-1387 (2009).
International Preliminary Report for International Application No. PCT/US14/64549 dated May 10, 2016.
International Preliminary Report on Patentability for International Application No. PCT/US2015/018118 dated Sep. 6, 2016.
International Preliminary Report on Patentability for International Application No. PCT/US2015/057538 dated May 2, 2017.
International Preliminary Report on Patentability for International Application No. PCT/US2016/039270 dated Dec. 26, 2017.
International Preliminary Report on Patentability for International Application No. PCT/US2016/054924 dated Apr. 3, 2018.
International Preliminary Report on Patentability for PCT/US2014/023386, dated Sep. 24, 2015.
International Preliminary Report on Patentability for PCT/US2014/48230, dated Feb. 4, 2016.
International Preliminary Reporton Patentability for PCT/US2015/044180, dated Feb. 23, 2017.
International Preliminary Report on Patentability for PCT/US2015/044303, dated Feb. 23, 2017.
International Preliminary Report on Patentability for PCT/US2015/14039, dated Aug. 11, 2016.
International Preliminary Report on Patentability for PCT/US2015/14044, dated Aug. 11, 2016.
International Preliminary Report on Patentability for PCT/US2015/14109, dated Aug. 11, 2016.
International Preliminary Report on Patentability for PCT/US2015/14120, dated Aug. 11, 2016.

(56) References Cited

OTHER PUBLICATIONS

International Search Report and Written Opinion for International Application No. PCT/US14/64549 dated Mar. 11, 2015.
International Search Report and Written Opinion for International Application No. PCT/US2015/018118 dated May 19, 2015.
International Search Report and Written Opinion for International Application No. PCT/US2015/057538 dated Jan. 21, 2016.
International Search Report and Written Opinion for International Application No. PCT/US2016/039270 dated Oct. 18, 2016.
International Search Report and Written Opinion for International Application No. PCT/US2016/054924 dated Sep. 5, 2017.
International Search Report and Written Opinion for PCT/US2014/023386, dated Jul. 9, 2014.
International Search Report and Written Opinion for PCT/US2014/14120, dated Apr. 23, 2015.
International Search Report and Written Opinion for PCT/US2014/48230, dated Jan. 30, 2015.
International Search Report and Written Opinion for PCT/US2015/044180, dated Nov. 5, 2015.
International Search Report and Written Opinion for PCT/US2015/044303, dated Dec. 31, 2015.
International Search Report and Written Opinion for PCT/US2015/059551, dated Jan. 13, 2016.
International Search Report and Written Opinion for PCT/US2015/059622, dated Mar. 30, 2016.
International Search Report and Written Opinion for PCT/US2015/14039, dated Apr. 23, 2015.
International Search Report and Written Opinion for PCT/US2015/14044, dated Apr. 23, 2015.
International Search Report and Written Opinion for PCT/US2015/14109, dated Jul. 6, 2015.
International Search Report and Written Opinion for PCT/US2016/051017, dated Jan. 10, 2017.
International Search Report and Written Opinion for PCT/US2016/051107, dated Nov. 22, 2016.
Kadota, et al. "Identification of Novel Gene Amplifications in Breast Cancer and Coexistence of Gene Amplification With an Activating Mutation of PIK3CA," Cancer Res, 69(18): 7357-7365 (2009).
Kavanagh et al., "The Development of CNS-active LRRK2 Inhibitors Using Property-directed Optimisation," Bioorg Med Chem Lett, 23(13): 3690-3696 (2013).
Kim, et al., "Berberine Improves Lipid Dysregulation in Obesity by Controlling Central and Peripheral AMPK Activity," Am J Physiol Endocrinol Metab, 296(4): E812-E819 (2009).
Konze et al., "An Orally Bioavailable Chemical Probe ofthe Lysine Methyltransferases EZH2 and EZH1," ACS Chem Biol, 8(6): 1324-1334 (2013).
Krueger et al., "The Mechanism of Release of P-TEFb and HEXIM1 from the 7SK snRNP by Viral and Cellular Activators Includes a Conformational change in 7SK," PLoS One, 5(8): e12335 (2010).
Lawless, et al., "Histone Deacetylase Inhibitors Target Diabetes Via Chromatin Remodeling or as Chemical Chaperones?" Curr Diabetes Rev, 5(3):201-209 (2009).
Ie Coutre, et al., "In vivo eradication of human BCR/ABL-positive leukemia cells with an ABL kinase inhibitor," J Natl Cancer Inst, 91(2): 163-168 (1999).
Lee et al., "Synergistic Effect of JG1 and Rapamycin for Treatment of Human Osteosarcoma," Int J Cancer, 136(9): 2055-2064 (2014).
Lee et al., "Synergistic effect of JQ1 and rapamycin for treatment of human osteosarcoma," Int J Cancer, 136(9):2055-2064 (2014).
Lee, et al., "Berberine, a Natural Plant Product, Activates AMP-Activated Protein Kinase with Beneficial Metabolic Effects in Diabetic and Insulin-Resistant States," Diabetes, 55(8): 2256-2264 (2006).
Lotti et al., "Ultrasound ofthe Male Genital Tract in Relation to Male Reproductive Health," Hum Reprod Update, 21(1): 56-83 (2015).
Marushige, "Activation of Chromatin by Acetylation of Histone Side Chains," Proc Natl Acad Sci, 73(11): 3937-3941 (1976).
Matzuk, et al., "Small-Molecule Inhibition of BRDT for Male Contraception," Cell, 150(4): 673-684 (2012).
McKeown et al., "Biased Multicomponent Reactions to Develop Novel Bromodomain Inhibitors," J Med Chem, 57(21): 9019-9027 (2014).
Meguro, et al., "Heterocycles. Vl.1) Synthesis of4H-s-Triazolo[4,3-α][1,4]benzodiazepines, Novel Tricyclic Psychosedatives," Chem Pharm Bull, 21(11): 2382-2390 (1973).
Meng-er, et al., "Use of All-Trans Retinoic Acid in the Treatment of Acute Promyelocytic Leukemia," Blood, 72(2): 567-572 (1988).
Mochizuki, et al., "The Bromodomain Protein Brd4 Stimulates G1 Gene Transcription and Promotes Progression to S Phase," J Biol Chem, 283(14): 9040-9048 (2008).
Moros et al., "Synergistic Anti-tumor Activity of Lenalidomide with the BET Bromodomain Inhibitor CPI203 in Bortezomib-resistant Mantle Cell Lymphoma," Leukemia 28(10): 2049-2059 (2014).
Moros et al., "Synergistic antitumor activity of lenalidomide with the BET bromodomain inhibitor CPI203 in bortezomib-resistant mantle cell lymphoma," Leukemia, 28: 2049-2059 (2014).
Niesen, et al., "The use of Differential Scanning Fluorimetry to Detect Ligand Interactions that Promote Protein Stability," Nat Protoc, 2(9): 2212-2221 (2007).
Nishimura et al., "Fertility and Reproduction Studies of Apafant (WEB 2086 BS) in Rats Dosed Orally," Oyo Yakuri/Pharmacometrics, 52(3/4): 185-200 (1996).
Notification Concerning Transmittal of International Preliminary Report on Patentability, International Application No. PCT/US2011/036647, Titled: "Compositions and Methods of Modulating Metabolism", dated Nov. 29, 2012.
Notification Concerning Transmittal of International Preliminary Report on Patentability, International Application No. PCT/US2011/036667, Titled: "Male Contraceptive Compositions and Methods of Use", dated Nov. 29, 2012.
Notification Concerning Transmittal of International Preliminary Report on Patentability, International Application No. PCT/US2011/036672, Titled: "Compositions and Methods for Treating Leukemia", dated Nov. 29, 2012.
Notification Concerning Transmittal of International Preliminary Report on Patentability, International Application No. PCT/US2011/036701, Titled: "Compositions and Methods for Treating Neoplasia, Inflammatory Disease and Other Disorders", dated Nov. 29, 2012.
Notification of Transmittal of the International Search Report and the Written Opinion of the International Searching Authority, International Application No. PCT/US11/36647, Titled: "Compositions and Methods of Modulating Metabolism", dated Aug. 17, 2011.
Notification of Transmittal of the International Search Report and the Written Opinion of the International Searching Authority, International Application No. PCT/US11/36667, Titled: "Male Contraceptive Compositions and Methods of Use", dated Aug. 15, 2011.
Notification of Transmittal of the International Search Report and the Written Opinion of the International Searching Authority, International Application No. PCT/US11/36672, Titled: "Compositions and Methods for Treating Leukemia", dated Jan. 27, 2012.
Notification of Transmittal of the International Search Report and the Written Opinion of the International Searching Authority, International Application No. PCT/US11/36701, Titled: "Compositions and Methods for Treating Neoplasia, Inflammatory Disease and Other Disorders", dated Feb. 1, 2012.
Owen, et al., "The Structural Basis for the Recognition of Acetylated Histone R4 by the Bromodomain of Histone Acetyltransferase Gcn5p," The EMBO Journal, 19(22): 6141-6149 (2000).
Patani, et al., "Bioisosterism: A Rational Approach in Drug Design," Chem Rev, 96(8): 3147-3176 (1996).
Phelps, et al., "Clinical Response and Pharmacokinetics from a Phase 1 Study of an Active Dosing Schedule of Flavopiridol in Relapsed Chronic Lymphocytic Leukemia," Blood, 113(12): 2637-2645 (2009).
Preisler, et al., "Assessment of c-myc Expression in Individual Leukemic Cells," Leuk Res, 12(6): 507-516 (1988).
Ptashne, "Binding Reactions: Epigenetic Switches, Signal Transduction and Cancer," Curr Biol, 19(6): R234-R241 (2009).
PubChem CID 5325760. Published Jan. 25, 2006.
PubChem CID-55504609. Created Jan. 25, 2012.

(56) References Cited

OTHER PUBLICATIONS

PubChem CID-56267130. Created Jan. 25, 2012.
PubChem SID 225027960. Available date/deposit date: Feb. 2, 2015.
PubChem SID 235048169. Feb. 13, 2015.
PubChem SID 235671906. Feb. 12, 2015.
Quinn, et al., "A homogeneous method for investigation of methylation-dependent protein-protein interactions in epigenetics," Nucleic Acids Res, 38(2): e11(1-10) (2010).
Rahl, et al., "c-Myc Regulates Transcriptional Pause Release," Cell, 141(3): 432-445 (2010).
Rhein et al., "CD11b is a Therapy Resistance and Minimal Residual Disease-Specific Marker in Precursor B-cell Acute Lymphoblastic Leukemia," Blood, 115(18): 3763-3771 (2010).
Roberts et al., "A Bead-Based Proximity Assay for BRD4 Ligand Discovery," Curr Protoc Chem Biol, 7(4): 263-278 (2015).
Santillan, et al., "Bromodomain and Histone Acetyltransferase Domain Specificities Control Mixed Lineage Leukemia Phenotype," Cancer Res, 66(20): 10032-10039 (2006).
Schindler, et al. "Structural mechanism for STI-571 Inhibition of Abelson Tyrosine kinase. Science," 289(5486): 1938-1942 (2000).
Schreiber, et al., "Signaling Network Model of Chromatin," Cell, 111(6): 771-778 (2002).
Schroder et al., "Two-pronged Binding with Bromodomain-containing Protein 4 Liberates Positive Transcription Elongation Factor B from Inactive Ribonucleoprotein Complexes," J Biol Chem, 287(2): 1090-1099 (2012).
Seyrig, et al., "Effects of a Chronic Administration of Two Benzodiazepines on Food Intake in Rats Given a Highly Palatable Diet," Pharmacology Biochemistry & Behavior, 25(4): 913-918 (1986).
Shang, et al., "The First Bromodomain of Brdt, a Testis-Specific Member of the BET SubFamily of Double-Bromodomain-Containing Proteins, is Essential for Male Germ Cell Differentiation," Development, 134: 3507-3515 (2007).
Smith et al., "The Bromodomain: A New Target in Emerging Epigenetic Medicine," ACS Chem Biol, 11(3): 598-608 (2016).
Tanaka et al., "Inhibitors of Emerging Epigenetic Targets for Cancer Therapy: A Patient Review (2010-2014)," Pharm Pat Anal, 4(4): 261-284 (2015).
Taskinen, et al., "A High Tumor-Associated Macrophage Content Predicts Favorable Outcome in Follicular Lymphoma Patients Treated with Rituximab and Cyclophosphamide-Doxorubicin-Vincristine-Prednisone," Clin Cancer Res, 13(19): 5784-5785 (2007).
Tse et al., "ABT-263: A Potent and Orally Bioavaliable Bcl-2 Family Inhibitor," Cancer Res, 68(9): 3421-3428 (2008).
Verma et al., "Identification of Potent, Selective, Cell-Active Inhibitors of the Histone Lysine Methyltransferase EZH2," ACS Med Chem Lett, 3(12): 1091-1096 (2012).
Vollmuth, et al., "Structures ofthe dual bromodomains of the P-TEFb-activating protein Brd4 at atomic resolution," J Biol Chem, 284(52): 36547-36556 (2009).
VonGoigtlander, et al., "Alprazolam: Review of Pharmacological, Pharmacokinetic and Clinical Data," Drug Dev Res, 6(1): 1-12 (1985).
Wang et al., "Activation of SOX2 Expression BRD4-NUT Oncogenic Fusion Drives Neoplastic Transformation in NUT Midline Carcinoma," Cancer Research, 74(12): 3332-3343 (2014).
Wang, et al., "A Seamless Trespass: Germ Cell Migration Across the Seminiferous Epithelium During Spermatogenesis," J Cell Biol, 178(4): 549-556 (2007).
Wang, et al., "Brd2 Disruption in Mice Causes Severe Obesity Without Type 2 Diabetes," Biochem J, 425(1): 71-83 (2010).
Wehner et al., "Effects of Natlizumab, an Alpha4 Integrin Inhibitor, on Fertility in Male and Female Guinea Pigs," Birth Defects Res B Dev Reprod Toxicol, 86(2): 108-116 (2009).
Yang, "Multisite Protein Modification and Intramolecular Signaling," Oncogene, 24:1653-1662 (2005).
Yang, et al., "AZD1152, a novel and selective aurora B kinase inhibitor, induces growth arrest, apoptosis, and sensitization for tubulin depolymerizing agent or topoisomerase II inhibitor in human acute leukemia cells in vitro and in vivo," Blood, 110(6): 2034-2040 (2007).
Yang, et al., "Brd4 recruits P-TEFb to chromosomes at late mitosis to promote G1 gene expression and cell cycle progression," Mol Cell Biol, 28(3): 967-976 (2008).
Yang, et al., "Recruitment of P-TEFb for Stimulation of Transcriptional Elongation by the Bromodomain Protein Brd4," Mol Cell, 16(4): 535-545 (2005).
You, et al., "Kaposi's sarcoma-associated herpesvirus latency-associated nuclear antigen interacts with bromodomain protein Brd4 on host mitotic chromosomes," J Virol, 80(18): 8909-8919 (2006).
You, et al., "Regulation of Aurora B Expression by the Bromodomain Protein Brd4," Mol Cell Biol, 29:5094-5103 (2009).
Zeng, et al., "Bromodomain: an Acetyl-lysine Binding Domain," FEBS Lett, 513(1): 124-128 (2002).
Zhang, et al., "Down-Regulation of NF-kB Transcriptional Activity in HIV-Associated Kidney Disease by BRD4 Inhibition," J Biol Chem, 287(34): 28840-28851 (2012).
Zhang, et al., "Down-Regulation of NF-kB Transcriptional Activity in HIV-Associated Kidney Disease by BRD4 Inhibition," J Biol Chem, 287(46): 38956 (2012).
Zhao, et al., "Research Development on Fusion Protein Transcription Factor siRNA Specifically Targeting Leukemia," Sciencepaper Online: 1-6 and J Med Res, 39(2): 6-9 (2010) (English-language translation entitled "Progress of Research on siRNA that Targets Leukemia Specific Transcription Regulation Factor Fusion Proteins," 1-10).
Zuber, et al., "RNAi Screen Identifies Brd4 as a Therapeutic Target in Acute Myeloid Leukaemia," Nature, 478(7370): 524-528 (2011), with "Supplementary Information" from www.nature.com/nature/journal/v478/n7370/extref/nature10334-s1.pdf, pp. 1-33.
Zuercher et al., "Identification and Structure-activity Relationship of Phenolic Acyl Hydrazones as Selective Agonists for the Estrogen-related Orphan Nuclear Receptors ERRbeta and ERRgamma," J Med Chem, 48(9): 107-109 (2005).
*Notice of Allowance for U.S. Appl. No. 15/886,559, "Compositions and Methods for Treating Neoplasia, Inflammatory Disease and Other Disorders," dated Apr. 23, 2019.
*Requirement for Restriction/Election for U.S. Appl. No. 15/886,559 dated Jul. 16, 2018.
Belkina, et al., "BET Protein Function Is Required for Inflammation: Brd2 Genetic Disruption and BET Inhibitor JQ1 Impair Mouse Macrophage Inflammatory Responses," J Immunol 190:3670-3678 (2013).
Bendas et al., "Cancer Cell Adhesion and Metastasis: Selectins, Integrins, and the Inhibitory Potential of Heparins," International Journal of Cell Biology, 2012:1-10 (2012).
Braun et al., "Preclinical Study of the Bromodomain Inhibitor OTX015 In Acute Myeloid (AML) and Lymphoid (ALL) Leukemias," Blood 122:4218 (2013).
Dittmann et al., "The Commonly Used PI3-Kinase Probe LY294002 Is an Inhibitor of BET Bromodomains," ACS Chem Biol, 9(2):495-502 (2014).
Gonzalez-Barrosa et al., "Mutations in UCP2 in Congenital Hyperinsulism Reveal a Role for Regulation of Insulin Secretion," PLoS One, 3(1): 1-8 (2008).
Laubli et al., "L-Selectin Facilitation of Metastasis Involves Temporal Induction of Fut7-Dependent Ligands at Sites of Tumor Cell Arrest," Cancer Res 66(3):1536-1542 (2006).
Loven et al., "Selective Inhibition of Tumor Oncogenes by Disruption of Super-Enhancers," Cell 153: 320-334 (2013).
Novus Biologicals, "CD11b Expression, Leukocyte Adhesion and the Innate Immune System," Nobusbio.com, (2011).
Oltersdorf et al., "An inhibitor of Bcl-2 family proteins induces regression of solid tumours," Nature, 435(7042):677-681 (2005).
Sawicki et al., "Normal Blood Pressure in Patients with Insulinoma Despite Hyperinsulinemia and Insulin Resistance," J Am Soc Neprhol, 3:S64-S68 (1992).
Shanik et al., "Insulin Resistance and Hyperinsulinemia," Diabetes Care, 31(2): S262-S268 (2008).

(56) References Cited

OTHER PUBLICATIONS

Trudel et al., "Preclinical studies of the pan-Bcl inhibitor obatoclax (GX015-070) in multiple myeloma," Blood, 109(12):5430-5438 (2007).

Vandenberg et al., "ABT-199, a new Bcl-2-specific BH3 mimetic, has in vivo efficacy against aggressive Myc-driven mouse lymphomas without provoking thrombocytopenia," Blood, 121(12):2285-2288 (2013).

Baker et al., "BET inhibitors induce apoptosis through a MYC independent mechanism and synergise with CDK inhibitors to kill osteosarcoma cells," Scientific Reports, 5:10120 (2015).

Bhadury et al., "BET and HDAC inhibitors induce similar genes and biological effects and synergize to kill in Myc-induced murine lymphoma," PNAS, 111(26): E2721-E2730 (2014).

Dickinson et al., "BET Inhibitor RG6146, Venetoclax, and Rituximab is a Highly Active Regimen in Relapsed/Refractory (R/R) DLBCL: Initial Report of Phase 1B Safety, Biomarker, and Response Data," Hematological Oncology, 37(S2): 174-175 (Abstract) (2019).

Dickinson et al., "ICML 2019 | RG6146 and venetoclax in DLBCL," LymphomaHub, Retrieved online <https://lymphomahub.com/medical-information/icml-2019-rg6146-and-venetoclax-in-dlbcl>: 4 pages (2019).

Fiskus et al., "BET Protein Antagonist JQ1 Is Synergistically Lethal with FLT3 Tyrosine Kinase Inhibitor (TKI) and Overcomes Resitance to FLT3-TKI in AML Cells Expressing FLT-ITD," Mol Cancer Ther; 13(10); 2315-27 (2014).

Gopalakrishnan et al., "Immunomodulatory drugs target IKZF1-IRF4-MYC axis in primary effusion lymphoma in a cereblon-dependent manner and display synergistic cytotoxicity with BRD4 inhibitors," Oncogene, 35: 1797-1810 (2016).

Lee et al., "Synergistic effect of JQ1 and rapamycin for treatment of human osteosarcoma," Int. J. Cancer, 136: 2055-2064 (2015).

Pérez-Salvia et al., "Bromodomain inhibitors and cancer therapy: From structures to applications," Epigenetics, 12(5): 323-339 (2017).

Sun et al., "Synergistic activity of BET protein antagonist-based combinations in mantle cell lymphoma cells sensitive or resistant to ibrutinib," Blood, 126(13): 1565-1574 (2015).

Tinsley et al., "Synergistic induction of cell death in haematological malignancies by combined phosphoinositide-3-kinase and BET bromodomain inhibition," British Journal of Haematology, 170:268-287 (2015).

\* cited by examiner

FIG. 3G
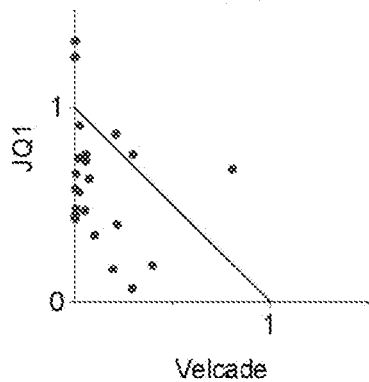
FIG. 3H
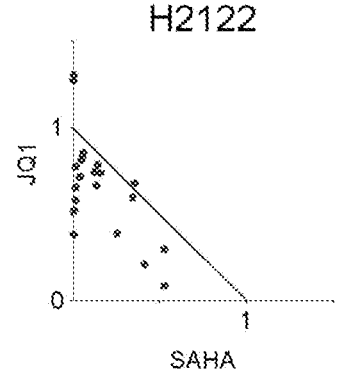
FIG. 4
FIG. 4A
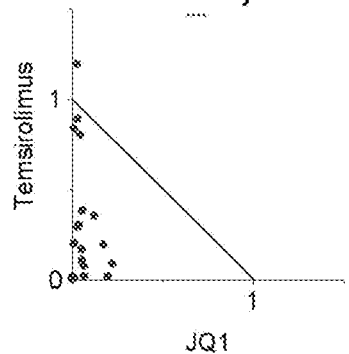
FIG. 4B
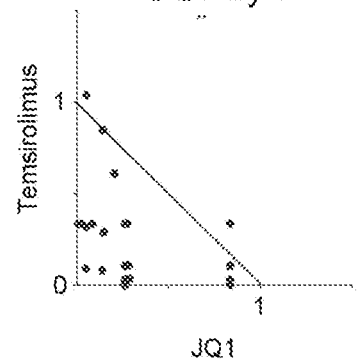
FIG. 4C
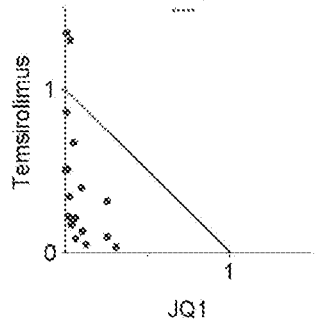
FIG. 4D
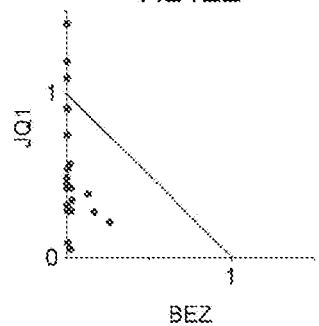

COMBINATION THERAPY FOR CANCER USING BROMODOMAIN AND EXTRA-TERMINAL (BET) PROTEIN INHIBITORS

RELATED APPLICATIONS

This application is a national stage filing under 35 U.S.C. § 371 of International Application No. PCT/US2014/064549, filed Nov. 7, 2014, and entitled "COMBINATION THERAPY FOR CANCER USING BROMODOMAIN AND EXTRA-TERMINAL (BET) PROTEIN INHIBITORS," which claims the benefit under 35 U.S.C. § 119(e) of U.S. Provisional Application No. 61/901,908, filed Nov. 8, 2013, the contents of each of which are incorporated by reference herein in their entirety.

GOVERNMENT SUPPORT

This invention was made with government support under grant numbers CA122794, CA140594, CA137181, CA137008, CA147940, U01 CA141576, and P50 CA090578 awarded by the National Institutes of Health. The government has certain rights in the invention.

BACKGROUND OF THE INVENTION

Cancers as a group account for approximately 13% of all deaths each year with the most common being: lung cancer (1.4 million deaths), stomach cancer (740,000 deaths), liver cancer (700,000 deaths), colorectal cancer (610,000 deaths), and breast cancer (460,000 deaths). The three most common childhood cancers are leukemia (34%), brain tumors (23%), and lymphomas (12%). Rates of childhood cancer have increased by 0.6% per year between 1975 to 2002 in the United States and by 1.1% per year between 1978 and 1997 in Europe. This makes invasive cancer the leading cause of death in the developed world and the second leading cause of death in the developing world.

Numerous anti-cancer drugs have been developed including kinase inhibitors, and anti-apoptotic agents. However, their toxicity to patients continues to be a major problem. For example, kinase inhibitors such as dasatinib and erlotinib are used in the treatment of cancer, but their adverse effects remains a serious problem. Dasatinib increases the risk of a rare but serious condition in which there is abnormally high blood pressure in the arteries of the lungs (pulmonary hypertension, PAH), while serious gastrointestinal tract, skin, and ocular disorders have been observed in patients taking the erlotinib. Furthermore, the clinical efficacy of kinase inhibitors is limited by the development of drug resistance. Accordingly, there is a need to identify novel and efficacious therapeutic strategies that mitigate the limitations of current anti-cancer drugs.

SUMMARY OF THE INVENTION

The present invention is based, at least in part, on the unexpected discovery that combinations of bromodomain and extra-terminal (BET) protein inhibitors and certain chemotherapeutic drugs are particularly effective at treating subjects with neoplasia. Thus, the present disclosure provides improved methods of treating neoplasia. According to some aspects of the invention, the method comprises administering to a subject in need thereof JQ1 and/or its analog in combination with a kinase inhibitor selected from the group consisting of MK2206, dasatinib, AZD6244, crizotinib, CYT387, Lapatinib, flavopiridol, y-27632, erlotinib, Afatinib, Axitinib, Bosutinib, cetuximab, Fostamatinib, Gefitinib, Imatinib, Lapatinib, Lenvatinib, Mubritinib, Nilotinib, Panitumumab, Pazopanib, Ruxolitinib, Sorafenib, Sunitinib, Trastuzumab, Vandetanib, and Vemurafenib in an amount effective to treat the neoplasia.

In some embodiments, the kinase inhibitor is selected from the group consisting of crizotinib, CYT387, Lapatinib, and flavopiridol. In some embodiments, JQ1 and/or its analog is administered separately, sequentially or simultaneously with the kinase inhibitor.

According to some aspects of the invention, methods of treating neoplasia are provided which comprise administering to a subject in need thereof JQ1 and/or its analog in combination with an anti-apoptotic agent in an amount effective to treat the neoplasia. In some embodiments, the anti-apoptotic agent is selected from the group consisting of ABT263, ABT199, ABT737, and obatoclax. In some embodiments, JQ1 and/or its analog is administered separately, sequentially or simultaneously with the anti-apoptotic agent.

According to some aspects of the invention, methods of treating neoplasia are provided which comprise administering to a subject in need thereof JQ1 and/or its analog in combination with an anti-neoplastic agent selected from the group consisting of vincristine, etoposide, 17-AAG, adrucil, velcade, SAHA, doxil, gemcitabine, AZD2281, DBZ, ifosfamide, revlimid, prednisone, rituximab, Bevacizumab, Pegaptanib, and Ranibizumab in an amount effective to treat the neoplasia. In some embodiments, the anti-neoplastic agent is velcade or gemcitabine. In some embodiments, JQ1 and/or its analog is administered separately, sequentially or simultaneously with the anti-neoplastic agent.

According to some aspects of the invention, methods of treating neoplasia are provided which comprise administering to a subject in need thereof an effective amount of JQ1 and/or its analog in combination with temsirolimus or BEZ235, wherein temsirolimus or BEZ235 is administered at a dose where it alone has no anti-neoplastic effect. In some embodiments, JQ1 and/or its analog is administered separately, sequentially or simultaneously with temsirolimus or BEZ235.

The following embodiments apply equally to the various aspects of the invention set forth herein unless indicated otherwise.

In some embodiments, the subject is a mammal. In some embodiments, the subject is a human patient. In some embodiments, the subject has neoplasia selected from the group consisting of selected from the group consisting of lung cancer, lymphomas including diffuse large B-cell lymphoma and Burkitt's lymphoma, prostate cancer, basal cell carcinoma, biliary tract cancer, bladder cancer, bone cancer, brain cancer, CNS cancer, breast cancer, cervical cancer, choriocarcinoma, colon cancer, rectum cancer, connective tissue cancer, cancer of the digestive system, endometrial cancer, esophageal cancer, eye cancer, cancer of the head and neck, gastric cancer, intra-epithelial neoplasm, kidney cancer, larynx cancer, leukemia, liver cancer, lung cancer, hematologic neoplasias, melanoma, myeloma, neuroblastoma, oral cavity cancer, ovarian cancer, pancreatic cancer, retinoblastoma, rhabdomyosarcoma, rectal cancer, renal cancer, cancer of the respiratory system, sarcoma, skin cancer, stomach cancer, testicular cancer, thyroid cancer, uterine cancer, and cancers of the urinary system. In some embodiments, the neoplasia is lung cancer. In some embodiments, the neoplasia is diffuse large B-cell lymphoma. In some embodiments, the neoplasia is Burkitt's lymphoma.

In some embodiments, the subject is further treated with an additional anti-neoplasia therapy. In some embodiments, the additional anti-neoplasia therapy is surgery, radiation therapy, chemotherapy, gene therapy, DNA therapy, viral therapy, RNA therapy, adjuvant therapy, immunotherapy or a combination thereof. In some embodiments, JQ1 and/or its analog is JQ1.

According to some aspects of the invention, pharmaceutical compositions are provided. These compositions comprise an effective amount of JQ1 or an analog thereof, and a kinase inhibitor selected from the group consisting of MK2206, dasatinib, AZD6244, crizotinib, CYT387, Lapatinib, flavopiridol, y-27632, erlotinib, Afatinib, Axitinib, Bosutinib, cetuximab, Fostamatinib, Gefitinib, Imatinib, Lapatinib, Lenvatinib, Mubritinib, Nilotinib, Panitumumab, Pazopanib, Ruxolitinib, Sorafenib, Sunitinib, Trastuzumab, Vandetanib, and Vemurafenib.

According to some aspects of the invention, a kit comprising a package containing a container containing JQ1 or an analog thereof, and a container containing a kinase inhibitor selected from the group consisting of MK2206, dasatinib, AZD6244, crizotinib, CYT387, Lapatinib, flavopiridol, y-27632, erlotinib, Afatinib, Axitinib, Bosutinib, cetuximab, Fostamatinib, Gefitinib, Imatinib, Lapatinib, Lenvatinib, Mubritinib, Nilotinib, Panitumumab, Pazopanib, Ruxolitinib, Sorafenib, Sunitinib, Trastuzumab, Vandetanib, and Vemurafenib is provided.

The details of particular embodiments of the invention are set forth herein. Other features, objects, and advantages of the invention will be apparent from the Detailed Description, the Figures, the Examples, and the Claims.

BRIEF DESCRIPTION OF THE DRAWINGS

FIG. 4 depicts isobolograms representing the additive effects between temsirolimus or BEZ235 and JQ1.

DETAILED DESCRIPTION OF THE INVENTION

Figure 1A:
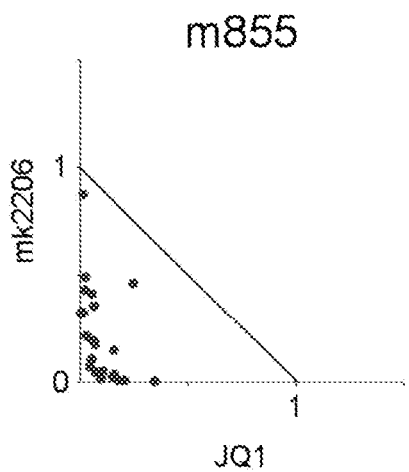
FIG. 1 depicts isobolograms demonstrating the synergy between kinase inhibitors and JQ1. Points below the 1 to 1 line connecting the X and Y axes are 'synergistic', points near the line are 'additive', and points above it are antagonistic.

The present invention is based, at least in part, on the surprising discovery that combinations of bromodomain and extra-terminal (BET) protein inhibitors and certain chemotherapeutic drugs are particularly effective at treating subjects with neoplasia. As demonstrated in the Examples described below, it has been found that the therapeutic efficacy of BET bromodomain inhibitor thieno-triazolo-1,4-diazepine (JQ1) and certain chemotherapeutics, such as specific kinase inhibitors, and anti-apoptotic agents, when administered in combination exhibit synergy. Thus, the combination of JQ1 and/or its analogs with certain kinase inhibitors, anti-apoptotic agents and other specific anti-neoplastic agents is more effective in treating neoplasia than the additive effects of the individual therapeutic agents.

The synergistic effect of the combination of therapeutic agents described herein permits the use of lower dosages of one or more of the therapeutic agent(s) and/or less frequent administration of the agent(s) to a subject with neoplasia. The ability to utilize a lower dosage of one or more therapeutic agent(s) and/or to administer the therapeutic agent(s) less frequently reduces the toxicity associated with the administration of the agent(s) to a subject without reducing the efficacy of the therapy in the treatment of neoplasia. In addition, the synergistic effect results in improved efficacy of the agents in the prevention, management or treatment of neoplasia. Finally, the synergistic effect of the combination of therapeutic agents described herein helps to avoid or reduce adverse or unwanted side effects associated with the use of either therapeutic agent alone.

The present invention provides methods for treating neoplasia using synergistic combinations of JQ1 and/or its analogs with certain kinase inhibitors, anti-apoptotic agents and other specific anti-neoplastic agents. As used herein, neoplasia means a disease state of a human or an animal in which there are cells and/or tissues which proliferate abnormally. A neoplasm can be benign, potentially malignant (pre-cancer), or malignant (cancer).

Examples of cancers that may be treated with the combinations described herein include, but are not limited to, solid tumors and hematological cancers. Solid tumors are exemplified by tumors of the breast, bladder, bone, brain, central and peripheral nervous system, colon, connective tissue, endocrine glands (e.g., thyroid and adrenal cortex), esophagus, endometrium, germ cells, head and neck, kidney, liver, lung, larynx and hypopharynx, mesothelioma, muscle, ovary, pancreas, penis, prostate gland, rectum, renal, small intestine, soft tissue, testis, stomach, skin, ureter, vagina, and vulva. Also included are inherited cancers exemplified by retinoblastoma and Wilms' tumor. In addition, primary tumors in said organs are included as well as corresponding secondary tumors in distant organs ("tumor metastases").

Hematological cancers are exemplified by aggressive and indolent forms of leukemia and lymphoma, namely diffuse large B cell lymphoma, non-Hodgkin's disease, chronic and acute myeloid leukemia (CML/AML), acute lymphoblastic leukemia (ALL), chronic lymphocytic leukemia (CLL), Hodgkin's disease, Burkitt's lymphoma, multiple myeloma, and T-cell lymphoma. Also included are myelodysplastic syndrome, plasma cell neoplasia, paraneoplastic syndromes, cancers of unknown primary site as well as AIDS-related malignancies.

Examples of benign neoplasms that may be treated with the combinations described herein include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

The BET (bromodomain and extra-terminal) proteins are four closely related bromodomain-containing proteins (BRD2, BRD3, BRD4, and BRDT) which constitute a subset of the larger family of 47 bromodomain-containing proteins. Bromodomains are acetyl-lysine binding pockets that target bromodomain-containing proteins to histones and thereby affect chromatin structure and function. The binding of BET protein bromodomains to chromatin regulates gene expression and small molecule inhibition of that binding produces selective effects on gene expression. Small molecule inhibition of BET bromodomains leads to selective killing of tumor cells across a broad range of hematologic malignancies and solid tumors. Non-limiting examples BET bromodomain inhibitors, known in the art, include JQ1 and its analogs which have been described in US 2013/0184264, the disclosure of which is incorporated herein by reference. Thus, in some embodiments, the methods, pharmaceutical compositions and kits of the present invention comprise the BET bromodomain inhibitors described in US 2013/0184264, and incorporated herein by reference. The present invention further encompasses pharmaceutically acceptable salts of such compounds. In some embodiments, the methods, pharmaceutical compositions and kits of the present invention comprise JQ1 or pharmaceutically acceptable salts thereof.

As used herein "kinase" refers to a large class of enzymes which catalyze the transfer of the γ-phosphate from ATP to the hydroxyl group on the side chain of Ser/Thr or Tyr in proteins and peptides and are intimately involved in the control of various important cell functions, perhaps most notably: signal transduction, differentiation and proliferation. There are estimated to be about 2,000 distinct protein kinases in the human body and although each of these phosphorylate particular protein/peptide substrates, they all bind the same second substrate ATP in a highly conserved pocket. About 50% of the known oncogene products are protein tyrosine kinases PTKs and their kinase activity has been shown to lead to cell transformation.

In some embodiments, JQ1 and/or its analog is administered in combination with kinase inhibitors selected from the group consisting of MK2206, dasatinib, AZD6244 (Selumetinib), crizotinib, CYT387, Lapatinib, flavopiridol, y-27632, erlotinib, Afatinib, Axitinib, Bosutinib, cetuximab, Fostamatinib, Gefitinib, Imatinib, Lapatinib, Lenvatinib, Mubritinib, Nilotinib, Panitumumab, Pazopanib, Ruxolitinib, Sorafenib, Sunitinib, Trastuzumab, Vandetanib, and Vemurafenib in an amount effective to treat the neoplasia. In some embodiments, the kinase inhibitor is selected from the group consisting of MK2206, dasatinib, AZD6244 (Selumetinib), crizotinib, CYT387, Lapatinib, and flavopiridol.

As shown in the Examples described below, a number of kinase inhibitors including MK2206, dasatinib, AZD6244 (Selumetinib), and crizotinib gave a synergistic response when administered in combination with JQ1. Without wishing to be bound by theory, kinases activate each other and similar pathways that then terminate in the nucleus where the signal is acted on by transcription factors. Since JQ1 targets BRD4 which is a critical adapter for many transcription factors, in view of the data described herein, a synergistic response is expected when the kinase inhibitors described herein are administered in combination with JQ1.

In some embodiments, JQ1 and/or its analog is administered in combination with an anti-apoptotic agent. As used herein, an anti-apoptotic agent is an agent that inhibits apoptosis. Such an agent can be a small organic or inorganic molecule. It may also be nucleic acid or peptide in nature. Non-limiting examples of anti-apoptotic agents include ABT263, ABT199, ABT737, ABT737, and obatoclax.

Without wishing to be bound by theory, it is hypothesized that while JQ1 strongly triggers G1 arrest, the anti-apoptotic inhibitors push the cells into full cell death. Thus, a synergistic response is expected when anti-apoptotic agents are administered in combination with JQ1.

In some embodiments, JQ1 and/or its analog is administered in combination with an anti-neoplastic agent selected from the group consisting of vincristine, etoposide, 17-AAG, adrucil, velcade, SAHA, doxil, gemcitabine, AZD2281 (Olaparib), DBZ, ifosfamide, revlimid (lenalidomide), prednisone, rituximab, Bevacizumab, Pegaptanib, and Ranibizumab in an amount effective to treat the neoplasia. In some embodiments, the anti-neoplastic agent selected from the group consisting of vincristine, etoposide, 17-AAG, adrucil, velcade and gemcitabine.

Without wishing to be bound by theory, it is hypothesized that since compounds that target DNA replication demonstrated a synergistic response with JQ1 (e.g., topoisomerase inhibitors such as etoposide), other compounds that target DNA replication such as doxil, AZD2281, and ifosfamid are also expected to exhibit a synergistic response when administered in combination with JQ1.

In some embodiments, JQ1 and/or its analog is administered in combination with temsirolimus or BEZ235, wherein temsirolimus or BEZ235 is administered at a dose where it alone has no anti-neoplastic effect. As demonstrated in the Examples described below, temsirolimus and BEZ235 increased the effect of JQ1 at doses where they alone have no effect. The recommended dose of temsirolimus is 25 mg IV infused over 30-60 minutes once per week. Thus, in some embodiments, temsirolimus is administered at a dose of 20 mg, 15 mg, 10 mg or 5 mg/week with JQ1, in some embodiments IV infused over 30-60 minutes once per week. In some embodiments, BEZ235 is administered at a dose of 50 mg; 100 mg; 150 mg; 200 mg; 250 mg; 300 mg; 350 mg; 400 mg; 450 mg; 500 mg; 650 mg; 700 mg; 750 mg; or 800 mg orally once daily with JQ1.

As used herein, the term "in combination" refers to the use of more than one therapeutic agent. The use of the term "in combination" does not restrict the order in which the therapeutic agents are administered to a subject with neoplasia. A first therapeutic agent, such as JQ1 or its analog, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent, such as a kinase inhibitor, anti-apoptotic agent or anti-neoplastic agent described herein, to a subject with neoplasia. Thus, JQ1 and/or its analog can be administered separately, sequentially or simultaneously with the second therapeutic agent, such as a kinase inhibitor, anti-apoptotic agent or anti-neoplastic agent described herein A "subject" to which administration is contemplated includes, but is not limited to, humans; commercially relevant mammals such as cattle, pigs, horses, sheep, goats, cats, and/or dogs) and birds (e.g., commercially relevant birds such as chickens, ducks, geese, and/or turkeys). A subject in need of treatment is a subject identified as having neoplasia, i.e., the subject has been diagnosed by a physician (e.g., using methods well known in the art) as having neoplasia. In some embodiments, the subject in need of treatment is a subject suspected of having or developing a neoplasia, such as a subject presenting one or more symptoms indicative of a neoplasia. The term "subject in need of treatment" further includes people who once had a neoplasia but whose symptoms have ameliorated. The one or more symptoms or clinical features of neoplasia depend on the type and location of the tumor. For example, lung tumors may cause coughing, shortness of breath, or chest pain. Tumors of the colon can cause weight loss, diarrhea, constipation, iron deficiency anemia, and blood in the stool. The following symptoms occur with most tumors: chills, fatigue, fever, loss of appetite, malaise, night sweats, and weight loss.

The terms "administer," "administering," or "administration," as used herein refers to implanting, absorbing, ingesting, injecting, or inhaling the one or more therapeutic agents.

As used herein, the terms "treatment," "treat," and "treating" refer to reversing, alleviating, delaying the onset of, or inhibiting the progress of neoplasia. In some embodiments, treatment may be administered after one or more signs or symptoms have developed or have been observed. In other embodiments, treatment may be administered in the absence of signs or symptoms of the neoplasia. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence.

An "effective amount" refers to an amount sufficient to elicit the desired biological response, i.e., treating the neoplasia. As will be appreciated by those of ordinary skill in this art, the effective amount of the compounds described herein may vary depending on such factors as the desired biological endpoint, the pharmacokinetics of the compound, the condition being treated, the mode of administration, and the age and health of the subject. An effective amount includes, but is not limited to, that amount necessary to slow, reduce, inhibit, ameliorate or reverse one or more symptoms associated with neoplasia. For example, in the treatment of neoplasia, such terms may refer to a reduction in the size of the tumor.

An effective amount of a compound may vary from about 0.001 mg/kg to about 1000 mg/kg in one or more dose administrations, for one or several days (depending on the mode of administration). In certain embodiments, the effective amount varies from about 0.001 mg/kg to about 1000 mg/kg, from about 0.01 mg/kg to about 750 mg/kg, from about 0.1 mg/kg to about 500 mg/kg, from about 1.0 mg/kg to about 250 mg/kg, and from about 10.0 mg/kg to about 150 mg/kg.

In some embodiments, the subject is further treated with one or more additional anti-neoplasia therapy. For example, the subject may undergo surgery, radiation therapy, chemotherapy, gene therapy, DNA therapy, viral therapy, RNA therapy, adjuvant therapy, immunotherapy or a combination thereof.

The compounds provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound, mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds provided herein may be administered at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

Pharmaceutical compositions described herein can be prepared by any method known in the art of pharmacology. In general, such preparatory methods include the steps of bringing the active ingredients such as JQ1 or an analog thereof into association with a carrier or excipient, and/or one or more other accessory ingredients, and then, if necessary and/or desirable, shaping, and/or packaging the product into a desired single- or multi-dose unit. Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The pharmaceutical preparations of the present invention may include or be diluted into a pharmaceutically-acceptable carrier. The term "pharmaceutically-acceptable carrier" as used herein means one or more compatible fillers, diluents or other such substances, which are suitable for administration to a human or other mammal such as a dog, cat, or horse. The term "carrier" denotes an organic or inorganic ingredient, natural or synthetic, with which the active ingredient is combined to facilitate the application. The carriers are capable of being commingled with the preparations of the present invention, and with each other, in a manner such that there is no interaction which would substantially impair the desired pharmaceutical efficacy or stability. Carriers suitable for oral, subcutaneous, intravenous, intramuscular, etc. formulations can be found in Remington's Pharmaceutical Sciences, Mack Publishing Company, Easton, Pa.

The present invention is further illustrated by the following Example, which in no way should be construed as further limiting. The entire contents of all of the references (including literature references, issued patents, published patent applications, and co pending patent applications) cited throughout this application are hereby expressly incorporated by reference.

EXAMPLES

Material and Methods

Compounds were profiled against H2122 human lung cancer line and m855 mouse GEM line containing p53/kRas mutations. Compounds were also profiled against diffuse large B-cell lymphoma cell lines OCI-Ly1, OCI-Ly3, OCI-Ly4, OCI-Ly7, S-DHL4, SU-DHL6, SU-DHL7, HBL1, K422, U2932 and Toledo, and against Burkitt's lymphoma cell lines Raji and Ca46.

Using a Biotek EL406, 50 uL of cell media containing 20-60,000 cells/ml was distributed into white 384-well Nunc plates (Thermo). Suspension cells then received compound immediately while adherent cells lines were given one hour to reattach to the surface of the plate prior to compound addition. The compounds to be tested were dissolved in DMSO and arrayed on 384 well compound storage plates (Greiner). Each compound plate received one compound in 5 point dose response approximately centered on the IC50 of the given compound for a given cell line.

Compound arrays were distributed to assay plates using a 100 nl 384 or 96-well pin transfer manifold on a Janus MDT workstation (Perkin Elmer). By pinning the 'forwards' compound directly and the 'reverse' compound plate backwards, a set of 8 replicates of all 5 by 5 compound concentrations was achieved in addition to each compound in quadruplicate 5 point dose response on its own.

After addition of compound, cell plates were incubated for 72 hr in a 370 C incubator. Cell viability was evaluated using ATPlite (Perkin Elmer) following manufacturer protocols. Data was analyzed in CalcuSyn utilizing the median effect principle of presented by Chou-Talalay and visualized using GraphPad Prism Software. Key parameters assessed were combination index and dose reduction index.

ATPlite Assay

Using a Biotek EL406, 50 uL of cell media containing 20-60,000 cells/ml was distributed into white 384-well Nunc plates (Thermo). Immediately after plating, compound dissolved in DMSO was distributed to plates using a 100 nl 384-well pin transfer manifold on a Janus MDT workstation (Perkin Elmer). Stocks were arrayed in 10 point quadruplicate dose response in DMSO stock in 384-well Greiner compound plates. After addition of compound, cell plates were incubated for 72 hr in a 370 C incubator. Cell viability was evaluated using ATPlite (Perkin Elmer) and data was analyzed using GraphPad Prism Software.

Figure 1B:
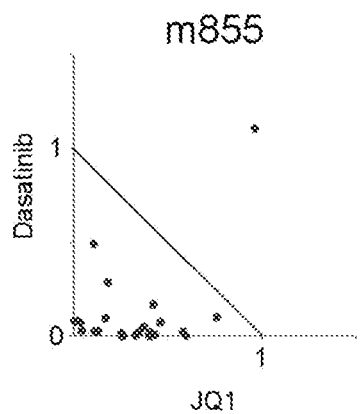
Figure 1C:
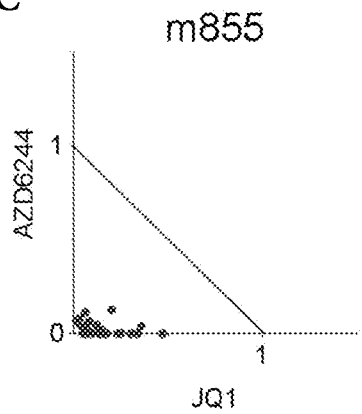
Figure 1D:
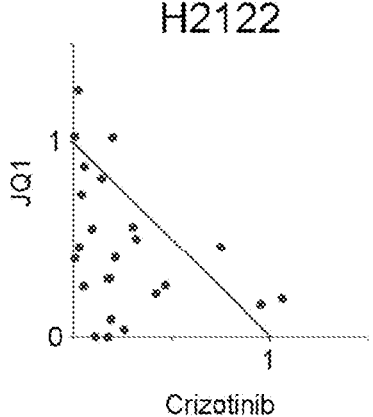
Figure 1E:
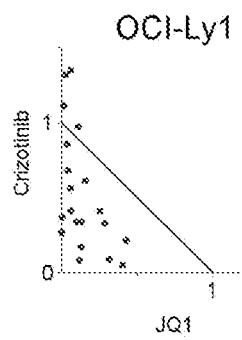
Figure 1F:
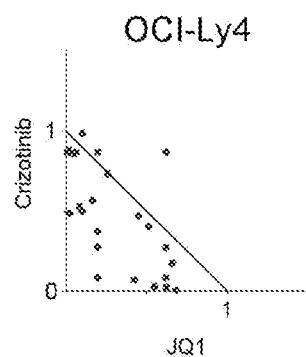
Figure 1G:
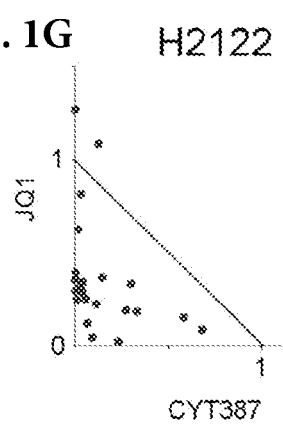
Figure 1H:
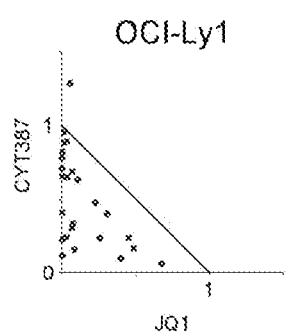
Figure 1I:
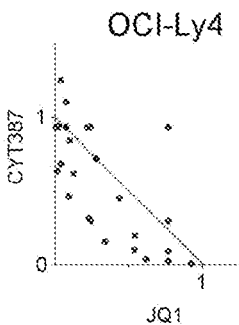
Figure 1J:
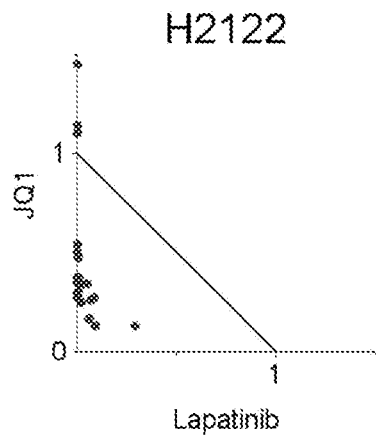
Figure 1K:
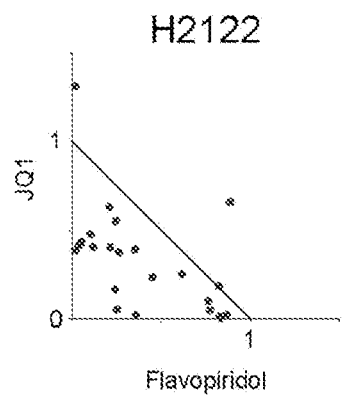
Figure 1K:
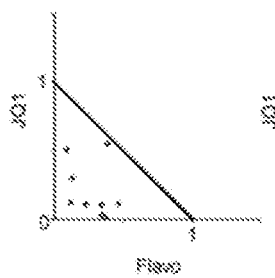
Figure 1K:
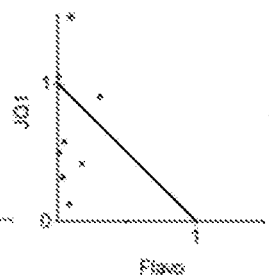
Figure 1K:
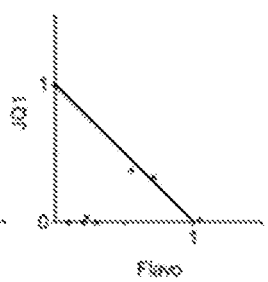
Figure 1K:
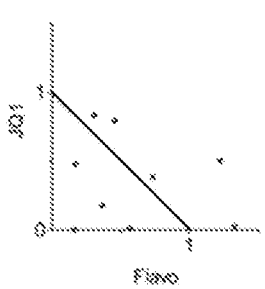

Results:

FIG. 1 depicts isobolograms demonstrating the synergy between kinase inhibitors and JQ1. Points below the 1 to 1 line connecting the X and Y axes are 'synergistic', points near the line are 'additive', and points above it are antagonistic.

Figure 2A:
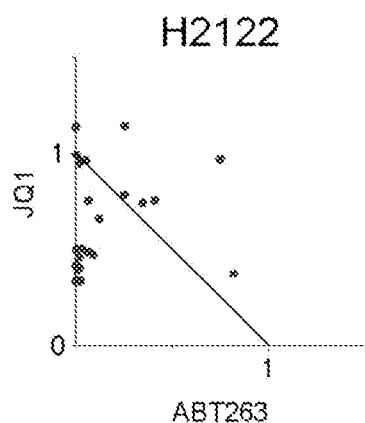
FIG. 2 depicts isobolograms representing the synergy between anti-apoptotic agents and JQ1.
Figure 2A:
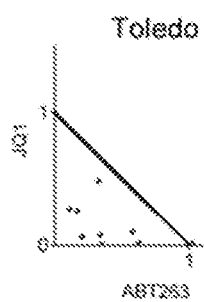
Figure 2A:
Figure 2A:
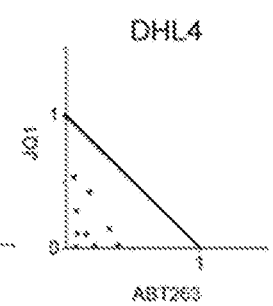
Figure 2A:
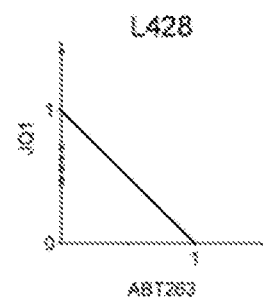
Figure 2A:
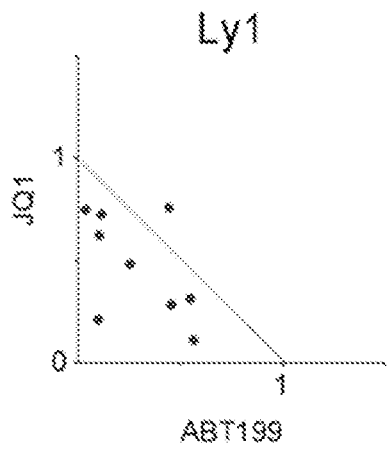
Figure 2A:
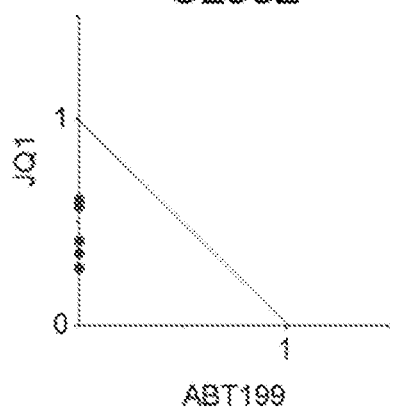
Figure 2H:
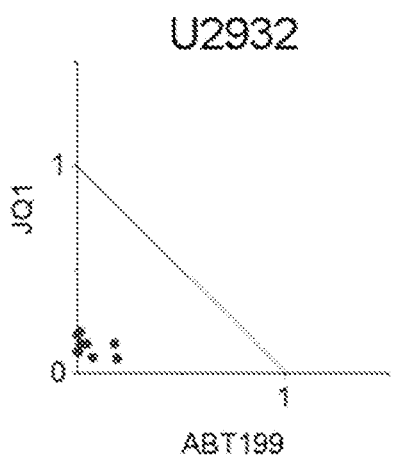
Figure 2I:
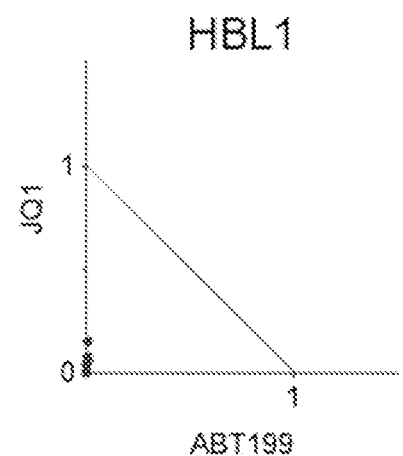
Figure 2J:
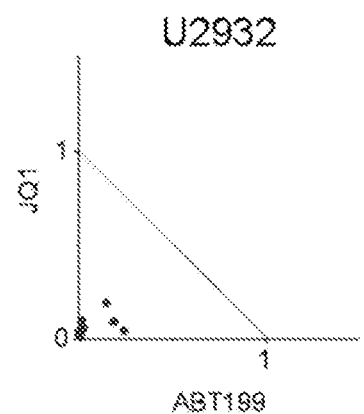
Figure 2K:
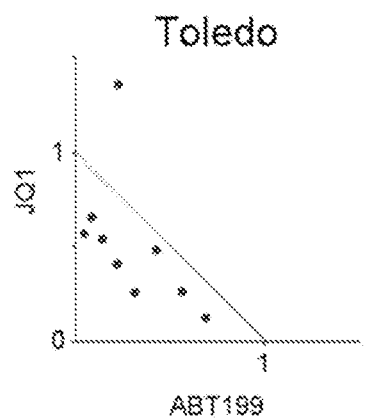
Figure 2L:
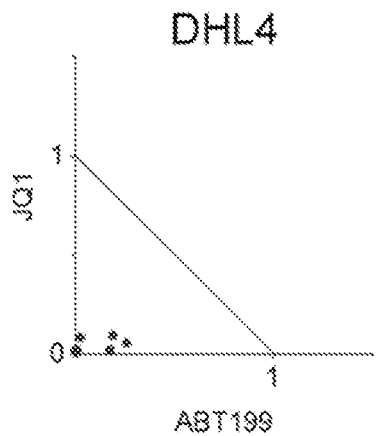
Figure 2M:
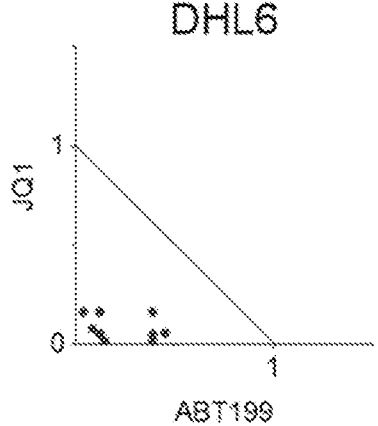

FIG. 2 depicts isobolograms representing the synergy between anti-apoptotic agents and JQ1.

Figure 3A:
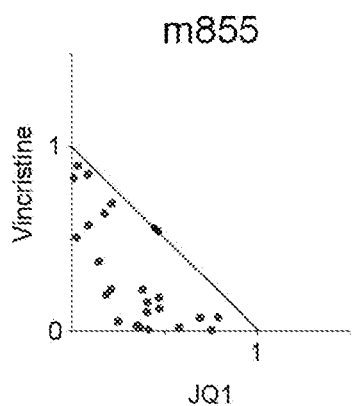
FIG. 3 depicts isobolograms representing the synergy between anti-neoplastic agents and JQ1.
Figure 3B:
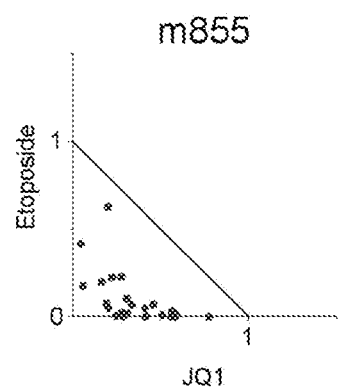
Figure 3C:
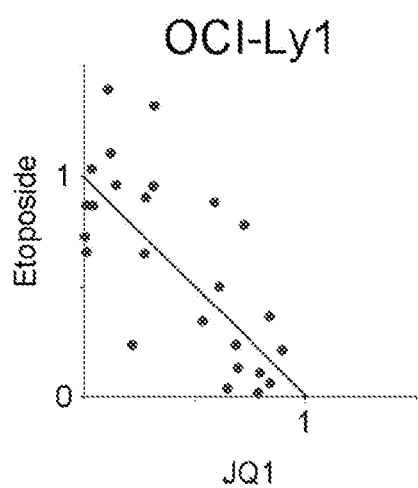
Figure 3D:
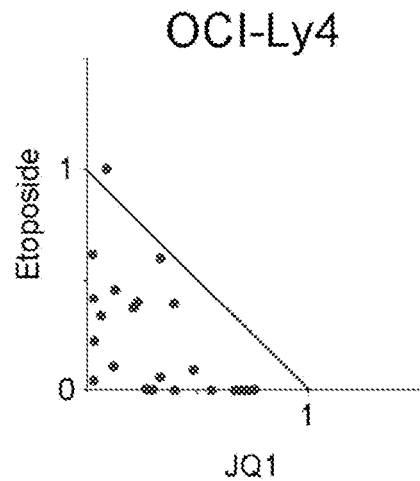
Figure 3E:
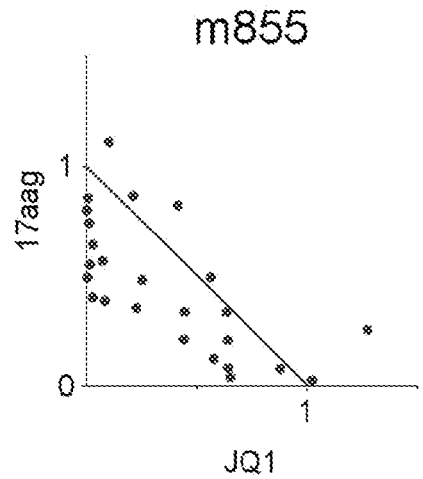
Figure 3F:
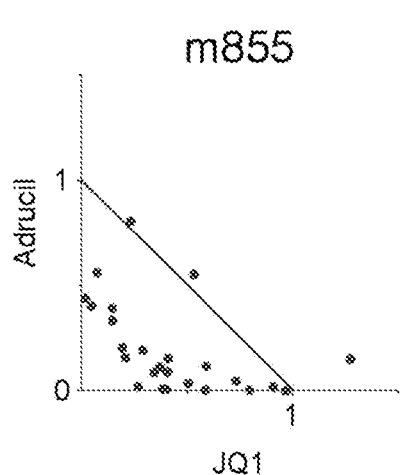

FIG. 3 depicts isobolograms representing the synergy between anti-neoplastic agents and JQ1.

FIG. 4 depicts isobolograms representing the additive effects between temsirolimus or BEZ235 and JQ1.

Figure 5A:
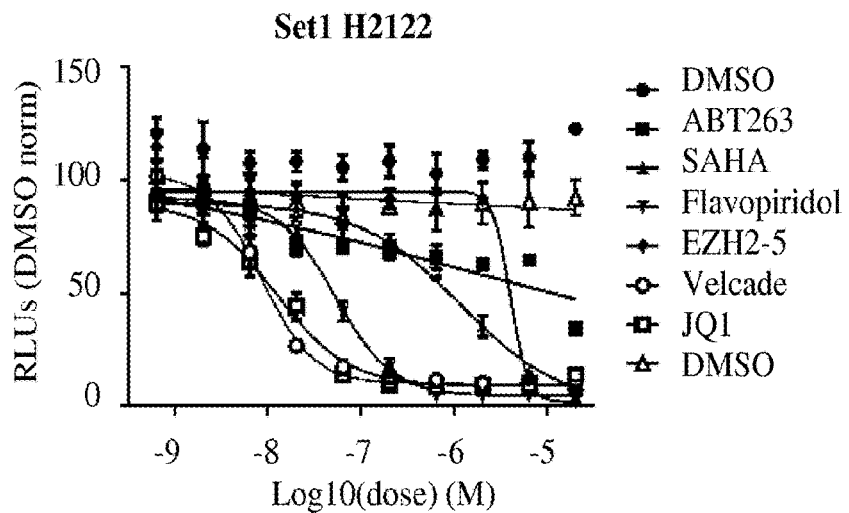
FIG. 5 shows the dose response curves for single agents.
Figure 5B:
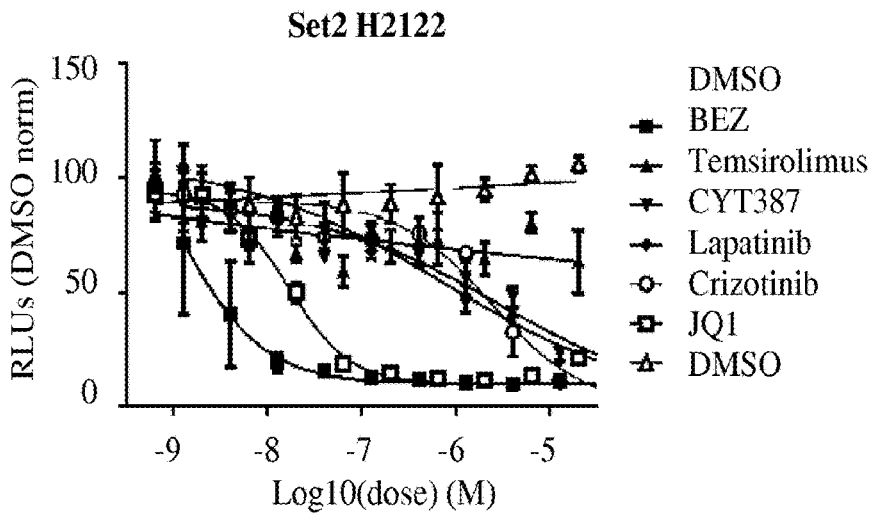
Figure 5C:
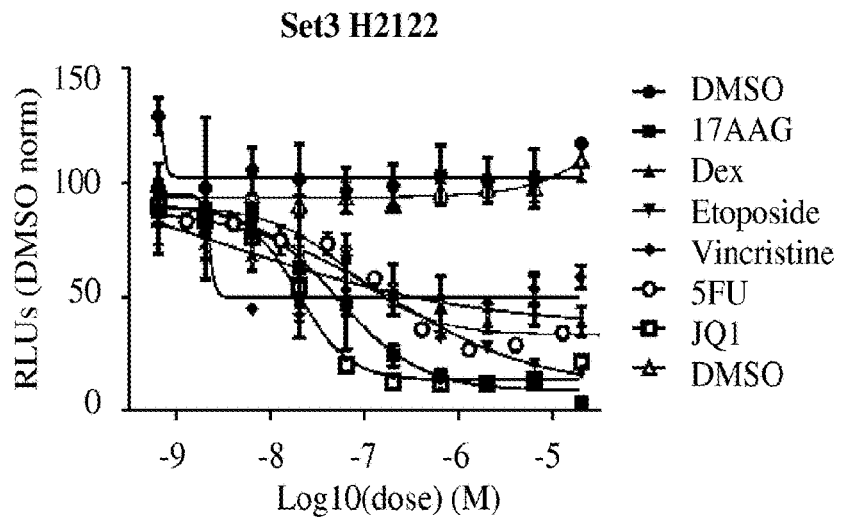
Figure 5D:
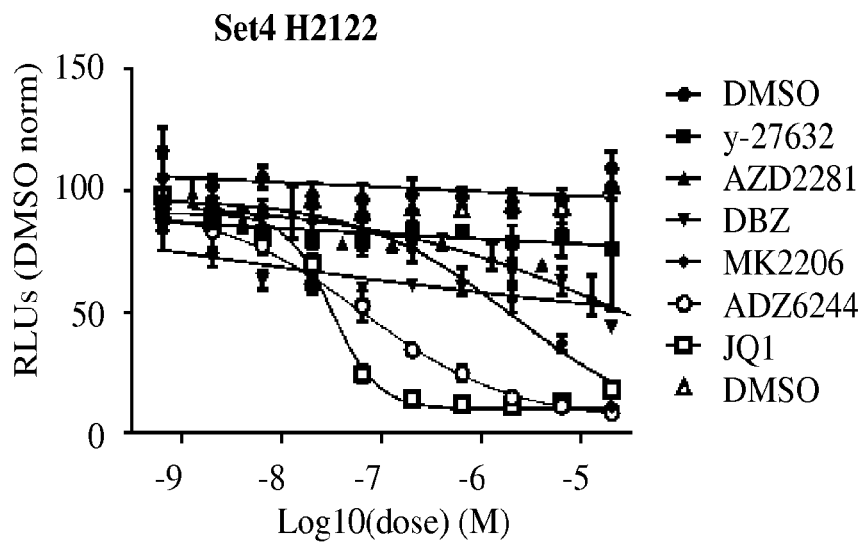
Figure 5E:
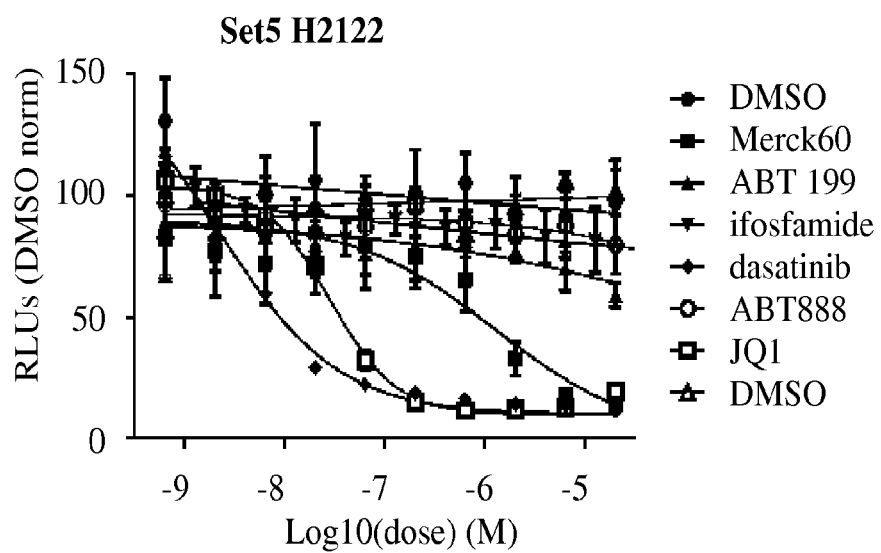

FIG. 5 shows the dose response curves for single agents.

TABLE 1

| | Average CI values for drug combinations | | | | | | | | | |
|---|---|---|---|---|---|---|---|---|---|---|
| | DHL4 | DHL6 | DHL7 | TOLEDO | LY4 | LY3 | HBL1 | RAJI | CA46 | L428 |
| JQ1/ABT263 | 0.341778 | 0.947889 | 0.550889 | 0.605 | 0.492444 | 0.624778 | 0.448889 | N/A | N/A | 2.756778 |
| JQ1/OBA | 0.852111 | 1.227556 | 1.083111 | 0.793333 | 0.859 | 0.821111 | 0.852222 | 0.442333 | 0.669889 | 0.742222 |
| JQ1/Flavo | 0.373889 | 0.657333 | 0.373889 | 1.418111 | 0.510111 | 0.641556 | 0.868 | 1.225222 | 1.709 | 2.419222 |
| Flavo/ABT263 | 0.496444 | 0.360222 | 1.429333 | 0.483778 | N/A | 1.480667 | 1.670667 | N/A | N/A | N/A |
| Flavo/OBA | 0.989889 | 0.969333 | 2.413333 | 0.692111 | 1.167889 | 0.32 | 1.899111 | 1.120222 | 0.768111 | 1.735333 |

Equivalents and Scope

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:

1. A method of treating diffuse large B-cell lymphoma (DLBCL) comprising:
administering to a subject in need thereof a first agent, S-JQ35:

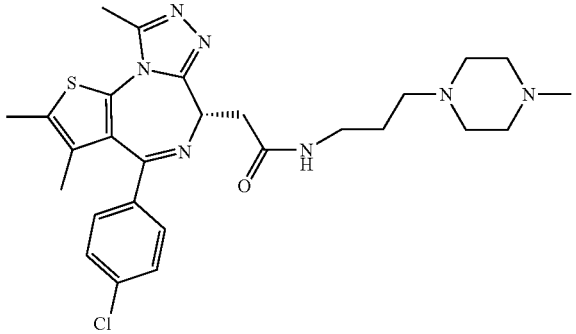

S-JQ35 or a pharmaceutically acceptable salt thereof,
in combination with one or more second agents selected from ABT263, or ABT199,
wherein the first agent and the one or more second agents are administered in an amount effective to treat the DLBCL.

2. The method of claim 1, wherein the first agent and the one or more second agents are administered sequentially or simultaneously.

3. The method of claim 1, wherein the subject is a mammal.

4. The method claim 3, wherein the subject is a human patient.

5. The method of claim 1, further comprising treating the subject with an additional anti-neoplasia therapy.

6. The method of claim 5, wherein the additional anti-neoplasia therapy is surgery, radiation therapy, chemotherapy, gene therapy, DNA therapy, viral therapy, RNA therapy, adjuvant therapy, immunotherapy or a combination thereof.

* * * * *